US012762473B2

(12) United States Patent
Chiang et al.

(10) Patent No.: US 12,762,473 B2
(45) Date of Patent: Oct. 13, 2026

(54) NETWORK-BASED FUNCTIONAL IMAGING OUTPUT FOR EVALUATING MULTIPLE SCLEROSIS

(71) Applicants: Board of Regents, The University of Texas System, Austin, TX (US); Texas State University, San Marcos, TX (US)

(72) Inventors: Florence Yi Yi Ling Chiang, San Antonio, TX (US); Peter T. Fox, San Antonio, TX (US); Rebecca S. Romero, San Antonio, TX (US); Larry Price, San Antonio, TX (US)

(73) Assignees: Board of Regents, The University of Texas System, Austin, TX (US); Texas State University, San Marcos, TX (US)

( * ) Notice: Subject to any disclaimer, the term of this patent is extended or adjusted under 35 U.S.C. 154(b) by 511 days.

(21) Appl. No.: 18/000,157

(22) PCT Filed: May 29, 2021

(86) PCT No.: PCT/US2021/070641
§ 371 (c)(1),
(2) Date: Nov. 29, 2022

(87) PCT Pub. No.: WO2021/243379
PCT Pub. Date: Dec. 2, 2021

(65) Prior Publication Data
US 2023/0263455 A1 Aug. 24, 2023

Related U.S. Application Data

(60) Provisional application No. 62/704,808, filed on May 29, 2020.

(51) Int. Cl.
*G06N 20/00* (2019.01)
*A61B 5/00* (2006.01)
(Continued)

(52) U.S. Cl.
CPC .......... *G06N 20/00* (2019.01); *A61B 5/0042* (2013.01); *A61B 5/055* (2013.01); *A61B 5/4064* (2013.01);
(Continued)

(58) Field of Classification Search
CPC ......... A61B 5/055; A61B 5/4064; A61B 5/72; A61B 5/0042; A61B 5/4088;
(Continued)

(56) References Cited

U.S. PATENT DOCUMENTS

2009/0279762 A1* 11/2009 Tsukimoto ....... G01R 33/56341 382/131
2013/0231552 A1 9/2013 Grady et al.
2016/0019693 A1 1/2016 Silbersweig et al.

FOREIGN PATENT DOCUMENTS

JP 2020062369 4/2020

OTHER PUBLICATIONS

Karrer, T. M., Bassett, D. S., Derntl, B., Gruber, O., Aleman, A., Jardri, R., . . . & Bzdok, D. (2019). Brain-based ranking of cognitive domains to predict schizophrenia. Human brain mapping, 40(15), 4487-4507. (Year: 2019).*

(Continued)

*Primary Examiner* — Keith M Raymond
*Assistant Examiner* — Johnathan Maynard
(74) *Attorney, Agent, or Firm* — Womble Bond Dickinson (US) LLP

(57) ABSTRACT

Provided here are non-invasive methods for evaluating functional connectivity patterns in localized brain regions of a patient involving application of a MS-specific functional meta-analytic connectivity model in resting-state functional magnetic resonance imaging (rsfMRI) data to provide patients with appropriate medical care in response to output from the model.

19 Claims, 18 Drawing Sheets

(51) Int. Cl.
*A61B 5/055* (2006.01)
*G01R 33/48* (2006.01)
*G01R 33/56* (2006.01)
*G01R 33/565* (2006.01)
*G06T 7/00* (2017.01)
*G16H 30/40* (2018.01)
*G16H 50/20* (2018.01)

(52) U.S. Cl.
CPC .............. *A61B 5/4088* (2013.01); *A61B 5/72* (2013.01); *G01R 33/5608* (2013.01); *G06T 7/0012* (2013.01); *G01R 33/4806* (2013.01); *G01R 33/5602* (2013.01); *G01R 33/56509* (2013.01); *G06T 2207/10088* (2013.01); *G06T 2207/30016* (2013.01); *G16H 30/40* (2018.01); *G16H 50/20* (2018.01)

(58) Field of Classification Search
CPC ........ A61B 5/7267; G06N 20/00; G06N 7/01; G01R 33/4806; G01R 33/5602; G01R 33/56509; G01R 33/5608; Y02A 90/10; G16H 30/40; G16H 50/20; G06T 2207/10088; G06T 2207/20072; G06T 2207/20081; G06T 2207/30016; G06T 7/0012
See application file for complete search history.

(56) References Cited

OTHER PUBLICATIONS

Chiang, F. L., Wang, Q., Yu, F. F., Romero, R. S., Huang, S. Y., Fox, P. M., . . . & Fox, P. T. (2019). Localised grey matter atrophy in multiple sclerosis is network-based: a coordinate-based meta-analysis. Clinical radiology, 74(10), 816-e19. (Year: 2019).*

Li, K., Laird, A. R., Price, L. R., McKay, D. R., Blangero, J., Glahn, D. C., & Fox, P. T. (2016). Progressive bidirectional age-related changes in default mode network effective connectivity across six decades. Frontiers in aging neuroscience, 8, 137. (Year: 2016).*

Kollndorfer, K., Krajnik, J., Woitek, R., Freiherr, J., Prayer, D., & Schöpf, V. (2013). Altered likelihood of brain activation in attention and working memory networks in patients with multiple sclerosis: an ALE meta-analysis. Neuroscience & Biobehavioral Reviews, 37(10), 2699-2708. (Year: 2013).*

Tewarie, P., Schoonheim, M., & Hillebrand, A. (2018). Structural and functional neuroimaging in multiple sclerosis: From atrophy, lesions to global network disruption. The neuroimaging of brain diseases: Structural and functional advances, 171-213. (Year: 2018).*

Hubbard, N. A., Hutchison, J. L., Turner, M. P., Sundaram, S., Oasay, L., Robinson, D., . . . & Rypma, B. (2016). Asynchrony in executive networks predicts cognitive slowing in multiple sclerosis. Neuropsychology, 30(1), 75. (Year: 2016).*

Yu, F. F., Chiang, F. L., Stephens, N., Huang, S. Y., Bilgic, B., Tantiwongkosi, B., & Romero, R. (2019). Characterization of normal-appearing white matter in multiple sclerosis using quantitative susceptibility mapping in conjunction with diffusion tensor imaging. Neuroradiology, 61, 71-79. (Year: 2019).*

Figueroa-Vargas, A., Cárcamo, C., Henríquez-Ch, R., Zamorano, F., Ciampi, E., Uribe-San-Martin, R., . . . & Billeke, P. (2020). Frontoparietal connectivity correlates with working memory performance in multiple sclerosis. Scientific Reports, 10(1), 9310. (Year: 2020).*

Keshavan, A. (2017). A neuroinformatics framework for the collection, curation, and visualization of imaging biomarkers in multiple sclerosis (Doctoral dissertation, UCSF). (Year: 2017).*

Bommarito, G. (2020). Novel functional imaging approaches for investigating brain plasticity in multiple sclerosis and Parkinson's disease: from research to clinical applications. (Year: 2020).*

Janssen, A. L. (2017). Physical Activity and Working Memory in Multiple Sclerosis: An Investigation of Neuropsychological and NeuroImaging Associations (Doctoral dissertation, The Ohio State University). (Year: 2017).*

Manglani, H. R. (2018). A neural network analysis of sedentary behavior and information processing speed in multiple sclerosis (Master's thesis, The Ohio State University). (Year: 2018).*

Lin, S. J. (2018). Advanced network analysis of resting-state functional connectivity to probe executive function in Parkinson's Disease and Multiple Sclerosis (Doctoral dissertation, University of British Columbia). (Year: 2018).*

Vigeveno, R. M., Wiebenga, O. T., Wattjes, M. P., Geurts, J. J., & Barkhof, F. (2012). Shifting imaging targets in multiple sclerosis: from inflammation to neurodegeneration. Journal of Magnetic Resonance Imaging, 36(1), 1-19. (Year: 2012).*

Hong, S. J., Lee, H. M., Gill, R., Crane, J., Sziklas, V., Bernhardt, B. C., . . . & Bernasconi, A. (2019). A connectome-based mechanistic model of focal cortical dysplasia. Brain, 142(3), 688-699. (Year: 2019).*

Duong, M. A., Boulanouar, K., Audoin, B., Treseras, S., Ibarrola, D., Malikova, I., . . . & Ranjeva, J. P. (2005). Modulation of effective connectivity inside the working memory network in patients at the earliest stage of multiple sclerosis. Neuroimage, 24(2), 533-538. (Year: 2004).*

Khazaee, A., Ebrahimzadeh, A., & Babajani-Feremi, A. (2015). Application of pattern recognition and graph theoretical approaches to analysis of brain network in Alzheimer's disease. Journal of Medical Imaging and Health Informatics, 5(6), 1145-1155. (Year: 2015).*

Khazaee, A., Ebrahimzadeh, A., & Babajani-Feremi, A. (2016). Application of advanced machine learning methods on resting-state fMRI network for identification of mild cognitive impairment and Alzheimer's disease. Brain imaging and behavior, 10(3), 799-817. (Year: 2016).*

Khazaee, A., Ebrahimzadeh, A., Babajani-Feremi, A., & Alzheimer's Disease Neuroimaging Initiative. (2017). Classification of patients with MCI and AD from healthy controls using directed graph measures of resting-state fMRI. Behavioural brain research, 322, 339-350. (Year: 2017).*

Khazaee, A., Ebrahimzadeh, A., & Babajani-Feremi, A. (2015). Identifying patients with Alzheimer's disease using resting-state fMRI and graph theory. Clinical Neurophysiology, 126(11), 2132-2141. (Year: 2015).*

Hojjati, S. H., Ebrahimzadeh, A., Khazaee, A., Babajani-Feremi, A., & Alzheimer's Disease Neuroimaging Initiative. (2017). Predicting conversion from MCI to AD using resting-state fMRI, graph theoretical approach and SVM. Journal of neuroscience methods, 282, 69-80. (Year: 2017).*

Subramanian, S., Rajamanickam, K., Prakash, J. S., Ramachandran, M., & Disease Neuroimaging Initiative, F. A. S. (2020). Study on structural atrophy changes and functional connectivity measures in Alzheimer's disease. Journal of Medical Imaging, 7(1), 016002-016002. (Year: 2020).*

European Search Report for EP Application No. 21814045.7, May 21, 2024.

International Search Report and Written Opinion for PCT/US2021/070641, Sep. 27, 2021.

Chiang. "Localised grey matter atrophy in multiple sclerosis is network-based: a coordinate-based meta-analysis". Clinical Radiology. [online]. Jul. 10, 2019; [Retrieved on Jul. 21, 2021). Retrieved from the internet: <url: http://website60s.com/upload/files/3-1ocalised-grey-matter-atrophy-in-multiple.pdf>; p. 816.e20, first column, second to last paragraph; p. 816.e20, second column, first and second paragraphs; DOI: 10.1016/j.crad.2019.07.005.

Tewarie. "Functional brain networks: Linking thalamic atrophy to clinical disability in multiple sclerosis, a multimodal fMRI and MEG Study". Human Brain Mapping. [online]. Oct. 8, 2014; vol. 36; pp. 603-618. [Retrieved on Jul. 21, 2021]. Retrieved from the internet: <url: https://www.ncbi.nlm.nih.gov/pmc/articles/PMC6869443/>; p. 606, second column; p. 607, first column, first paragraph.

Marco. "Principle of Structural Equation Modeling for Exploring Functional Interactivity within a Putative Network of Interconnected Brain Areas". Magnetic Resonance Imaging, Elsevier. (online].

(56) References Cited

OTHER PUBLICATIONS

2009; vol. 26, No. 1. (Retrieved on Jul. 22, 2021. Retrieved from the internet: <url: https://core.ac.uk/download/pdf/78772934.pdf>; p. 8, second column, third and fourth paragraphs; p. 10, first column, third paragraph; DOI: 10.1016/j.mri.2008.05.003.

Sondhi. "The Reduced PC-Algorithm: Improved Causal Structure Learning in Large Random Networks" . . . [online]. Sep. 24, 2019; [Retrieved on Jul. 23, 2021). Retrieved from the internet: <url: https://arxi'!.org/pdf/1806.06209.pdf>; abstract; p. 5, last paragraph.

Melville. "Functional connectivity model identifies MS impairment". Multiple Sclerosis Hub. [online]. Feb. 29, 2020; [Retrieved on Jul. 22, 2021). Retrieved from the internet: <url:https://www.mdedge.com/multiplesclerosishub/article/218128/mulliple-sclerosis/functional-connectivity-model-identifies-ms>; p. 1, second paragraph; p. 3, fourth paragraph; p. 4, last paragraph.

Marzullo. "Deep Learning and Graph Theory for Brain Connectivity Analysis in Multiple Sclerosis" . . . [online). Jan. 16, 2020; (Retrieved on Jul. 23, 2021). Retrieved from the internet: <url: https://tel.archives-ouvertes.fr/tel-02479670/document>; p. 71, last four paragraphs; p. 76, last paragraph; p. 81, last two paragraphs; p. 83, last paragraph.

* cited by examiner

NETWORK-BASED FUNCTIONAL IMAGING OUTPUT FOR EVALUATING MULTIPLE SCLEROSIS

REFERENCE TO RELATED APPLICATIONS

The present Patent Application claims the benefit of and priority to the U.S. Provisional Patent Application No. 62/704,808, filed May 29, 2020.

INCORPORATION BY REFERENCE

The disclosure of U.S. Provisional Patent Application No. 62/704,808, filed May 29, 2020, is specifically incorporated by reference herein as if set forth in its entirety.

GOVERNMENT SUPPORT

This invention was made with government support under grant numbers MH074457 and EB016631 awarded by the National Institutes of Health. The government has certain rights in the invention.

TECHNICAL FIELD

The disclosure relates to methods and systems for diagnosing and monitoring multiple sclerosis (MS) using diagnostic imaging. More specifically, the methods and systems include input from magnetic resonance imaging (MRI).

BACKGROUND

MS is a neurodegenerative disease that is characterized by separate attacks, in time and space, on the central nervous system (CNS), which leads to neurological disabilities and impairments. The underlying cause of this disease remains unknown; however, it is believed that MS is the result of a complex interactions, with some component of both genetic susceptibility and environmental factors. The complex nature of MS has created challenges for physicians trying to diagnose, manage, and understand the disease. Despite differences in the initial clinical diagnosis, MS patients are grouped into four major categories based on the disease course. These categories are relapsing-remitting multiple sclerosis (RRMS), secondary progressive multiple sclerosis (SPMS), primary progressive multiple sclerosis (PPMS), and progressive relapsing multiple sclerosis (PRMS). These four categories have differing disease courses and susceptibilities. Currently, MS remains a clinical diagnosis supported by MRI, laboratory findings from CSF (oligoclonal bands and raised IgG index), and evoked potential studies (electrical activity in the brain in response to stimulation of sight, sound, or touch). Diagnosis of MS is further complicated by several conditions that can mimic the features of MS, such as Lyme disease and lupus erythematosus. Because of this, cautious physicians may delay initiating treatment in patients while attempting to confirm the diagnosis; thus, restricting the window of opportunity for optimal therapy.

The most utilized diagnostic tools for diagnosing and monitoring MS are MRI (81%), CSF testing (53%) and evoked potentials (23%). However, clinical MRI methods focus primarily on characterization of demyelinating lesions, such as enhancement patterns, for diagnosis, which show limited correlation with disease progression. These limitations in patient management have prompted further research to elucidate the pathophysiology of MS to develop more sensitive diagnostic techniques to diagnose and monitor patients.

SUMMARY

Provided here are systems and methods to address these shortcomings of the art and provide other additional or alternative advantages. Provided here are non-invasive methods for evaluating altered functional connectivity involving localized brain regions prone to exhibiting neurodegeneration in a subject using resting-state functional magnetic resonance imaging (fMRI) data. A meta-analytic model of disease-affected regions and their connectivity was developed and this model was applied on a per-subject basis to primary fMRI data.

Functional imaging enables analysis of functional connectivity, with detection of functional abnormalities being more sensitive than structural abnormalities to detect neurodegeneration. Functional network properties related to localized grey matter atrophy in MS is a biomarker for early and accurate diagnosis of MS as well as continued monitoring. A functional network structure for assessing grey matter connectivity and localized neuro-degeneration-atrophy-based functional network (AFN) model was developed. Based on the AFN model, Network-based Functional Imaging Output in Multiple Sclerosis (NETFIO-MS) was constructed as a medical image analysis tool for application in resting-state functional magnetic resonance imaging (rsfMRI), which enables per-patient quantification of functional network-based disease burden in MS to aid in accurate diagnosis and monitoring of disease progression.

Resting-state functional magnetic resonance imaging (rsfMRI) serves as the input data, and the outputs include metrics of functional connectivity, such as model fit statistics and path correlation coefficients. The input for NETFIO-MS includes acquisition (e.g., as an input or via the preprocessing of an input) of three whole-brain MRI sequences: rsfMRI to demonstrate the blood-oxygen-level dependent (BOLD) signal, a gradient-echo fieldmap for distortion correction of rsfMRI, and a T1-weighted image for image registration during image preprocessing. The preprocessing pipeline can include one or more processes, such as motion correction, B0 unwarping, slice timing correction, and spatial smoothing. Additional noise-reduction steps can include independent component analysis-based cleanup (e.g. ICA-AROMA) and nuisance regression. After image preprocessing, the regions-of-interest (ROI) specified by AFN nodes are used to extract the mean timeseries data. The edges specified by the AFN model are used to define the functional connectivity for path coefficient computation.

The network structure of NETFIO-MS was meta-analytically derived from AFN. In an embodiment, the AFN is a method for determining the spatial convergence of results from published neuroimaging papers. Here, the AFN model leverages the large volume of existing literature and is not biased toward any particular dataset, considering a robust amount of disease variation between patients. The construction of the AFN model used the BrainMap neuroimaging database and consists of two components: "nodes" defined by regions of localized grey matter atrophy in MS, and "edges" defined by healthy functional connectivity involving the specified nodes (i.e. regions of grey matter atrophy in MS).

The nodes were determined by using differences in local concentrations of brain tissue (voxel-based morphometry) between a number of MS diagnosed subjects and another number of healthy control (HC) subjects. The edges were computed by using functional imaging results (task-activation fMRI and PET) from a large number of HC subjects. The AFN model was subsequently tested using rsfMRI. The results from this validation study were used to construct NETFIO-MS. The output paths are defined by the functional connectivity between the nodes (i.e. AFN edges). The path analysis computes standardized semi-partial regression coefficients for each AFN edge based on maximum likelihood estimation. The overall model fit statistics are computed to demonstrate the degree of AFN model fit to the rsfMRI. The root mean square error of approximation (RMSEA) is utilized as the primary fit criterion given its relative insensitivity to the effects of sample size; an RMSEA of <0.08 indicates a reasonably good fit to the data.

In this embodiment that includes the validation analysis with age and sex-matched HC, the diagnostic accuracy ranged from acceptable to excellent, AUC=0.805 without incorporation of lag variables and AUC=0.798 with incorporation of lag variables. The model fit statistic of RMSEA tracks disease progression, strongly correlating with the EDSS score (r=0.66) and moderately with disease duration (r=0.32). Alternatively, the normalized lesion volume (NLV) of white matter correlated weakly with both EDSS (r=−0.19) and disease duration (r=0.15). As the dataset, including MS subjects and HC subjects, increases, outputs (e.g., AUC, RMSEA, NLV, and/or other outputs) may vary.

An embodiment of a method for diagnosing multiple sclerosis includes the steps of acquiring blood-oxygen-level dependent (BOLD) resting-state functional magnetic resonance imaging (rsfMRI) data of a brain of a subject; applying an atrophy-based functional network (AFN) model in the rsfMRI data; and providing a diagnosis of multiple sclerosis in response to presence of altered functional connectivity involving localized brain regions in the subject based on the AFN model. In an embodiment, the altered functional connectivity involving localized brain regions is determined by meta-analysis of a gray-matter atrophy pattern of multiple sclerosis from the AFN model and a set of functional co-activation patterns of healthy controls. In an embodiment, a root mean square error of approximation of the AFN model is used to quantify multiple sclerosis-associated neurodegeneration. In an embodiment, structural equation modeling (SEM) edge weights of the AFN model is used to quantify multiple sclerosis-associated neurodegeneration.

An embodiment of a method for monitoring progression of multiple sclerosis includes the steps of acquiring blood-oxygen-level dependent (BOLD) resting-state functional magnetic resonance imaging (rsfMRI) data of a brain of a subject; applying an atrophy-based functional network (AFN) model in the rsfMRI data; and acquiring a first set of functional connectivity patterns involving localized brain regions based on the AFN model; and comparing the first set of functional connectivity patterns to previously acquired sets of functional connectivity patterns involving localized brain regions of the subject to determine changes in the functional connectivity patterns and monitor progression of multiple sclerosis in in the subject. In an embodiment, the changes in the functional connectivity patterns are used to assess response of the subject to a particular treatment regimen.

Provided here are non-invasive methods for detecting altered functional connectivity involving localized brain regions prone to exhibiting neurodegeneration in a subject. One such method includes the steps of acquiring whole-brain resting-state functional magnetic resonance imaging (rsfMRI) data; subjecting the rsfMRI data to distortion correction by applying a gradient-echo fieldmap; subjecting the rsfMRI data to motion correction; acquiring a T1-weighted image for image registration during image preprocessing; sampling regions of the brain of a subject specified by the nodes of an atrophy-based functional network (AFN) model; developing a functional network model in MS by applying the AFN model to the preprocessed rsfMRI data; and evaluating presence of altered functional connectivity in the brain of the subject based on the AFN model. In an embodiment, the rsfMRI data includes a blood-oxygen-level dependent (BOLD) signal. The AFN model has nodes and edges representing localized regions of grey matter atrophy and inter-regional functional connectivity. A root mean square error of approximation of the AFN model indicates progression of multiple sclerosis. The root mean square error of approximation is about 0.069. Diagnostic criteria of NETFIO-MS are based on edge weights rather than the root mean square error of approximation model fit statistic. Diagnosis is performed with logistic regression to binarize the group separation at different thresholds. The prediction accuracy is expressed as the AUC and is expected to improve with larger sample sizes. A diagnostic threshold value can be determined by using logistic regression on path coefficients (edge weights).

In another embodiment, a method for diagnosing and addressing multiple sclerosis (MS) is provided. The method may include acquiring an input. The input may include functional MRI (rsfMRI) data of a brain of a subject. The method may include preprocessing the input via motion correction, B0 warping, slice timing correction, and spatial smoothing. Such preprocessing may form a preprocessed input including gradient-echo fieldmap data of the rsfMRI data and T1-weighted data. The method may include applying the preprocessed input to an atrophy-based functional network (AFN) model to thereby form an output. The method may include, based on the output, providing a diagnosis of MS in response to presence of altered functional connectivity involving localized brain regions in the subject based on the application of the preprocessed input to the AFN model.

In other embodiments, the altered functional connectivity involving localized brain regions may be determined by meta-analysis of a gray-matter atrophy pattern of MS from the AFN model and a set of functional co-activation patterns of healthy controls. A root mean square error of approximation of the AFN model may be used to quantify MS-associated neurodegeneration. A structural equation modeling (SEM) edge weights of the AFN model may be used to quantify MS-associated neurodegeneration. In another embodiment, the altered functional connectivity is determined by machine learning algorithms trained using a dataset including subjects with a known diagnosis.

The method may further include determining a treatment regimen based on the output and diagnosis of MS. The method may include transmitting the treatment regimen to a user. The input may be acquired from a MRI device or from a user interface (e.g., rsfMRI provided to the AFN model via a user interface from a client device or other device). In another embodiment, the data utilized for training may be obtained from a research database (e.g., BrainMap neuroimaging database), a medical records or hospital database, a MRI database, another source of rsfMRI data, and/or some combination thereof. A treatment regimen can include one or more of a pharmaceutical product, such as alemtuzumab, azathioprine, cyclophosphamide, fingolimod, glatiramer acetate, immunoglobulins, interferon beta-la, mitoxantrone, mycophenolate mofetil, natalizumab, ocrelizumab, pegylated interferon, rituximab, or teriflunomide.

In another embodiment, a system to select a treatment regimen for diagnosing and addressing multiple sclerosis (MS) of a subject is provided. The system may include a magnetic resonance imaging (MRI) device to provide an input including resting-state functional MRI (rsfMRI) data. The system may include a Network-based Functional Imaging Output in Multiple Sclerosis (NETFIO-MS) device connected to and in signal communication with the MRI device and including an AFN model. The NETFIO-MS device may be configured to receive the input from the MRI device. The NETFIO-MS device may be configured to preprocess the input to thereby form a preprocessed input including one or more of gradient-echo fieldmap data of the rsfMRI data and T1-weighted data. The NETFIO-MS device may be configured to apply the input to the AFN model. The NETFIO-MS device may further be configured to, based on application of the input to the AFN model, provide an output including metrics of functional connectivity, the metrics of functional connectivity indicating diagnosis of MS in a subject. The NETFIO-MS device may be configured to, based on the output, determine a treatment regimen for the subject. The NETFIO-MS device may be configured to transmit the output and treatment regimen to a user.

In another embodiment, the system may, rather than including an MRI device, connect to an MRI device or may receive rsfMRI data from a client device, other system device, or other computing device. The NETFIO-MS device may include one or more processors and a non-transitory machine readable storage medium. The non-transitory machine readable storage medium may store the AFN model and instructions, which when executed by the processor, configured to apply the received input to the AFN model and determine the treatment regime In another embodiment, the rsfMRI indicates a blood-oxygen-level dependent (BOLD) signal.

In an embodiment, the AFN model may be a meta-analytical model. In another embodiment, the AFN Model may be a machine-learning model or may be based on a machine-learning model. In such embodiments, the AFN model may be trained to determine the output based on one or more sets of data, the one or more sets of data including a set of images, data, or video from subjects not exhibiting MS and a set of images, data, or video from subjects exhibiting various stages of MS. The AFN model may be trained to determine whether an image includes nodes and connectivity between the nodes which indicate MS, potential for development of MS, and/or progression or current stage of MS.

In an embodiment, the output may include an image of the subject's brain, the image including highlighted sections indicating the nodes and connectivity between the nodes. The output may be utilized to track progression of MS in a subject diagnosed with MS and, based on progression of MS in the subject diagnosed with MS, the NETFIO-MS device further be configured to update a previously determined treatment regimen. The NETFIOS-MS device may further be configured to transmit the updated treatment regimen to the user. The output of the AFN model may indicate progression of MS based on response to a previous treatment regimen and/or other factors.

In another embodiment, a non-transitory machine-readable storage medium storing processor-executable instructions that, when executed by at least one processor, cause the at least one processor to execute the instructions. The executed instructions may, in response to receipt of an input including resting-state functional MRI (rsfMRI) data, preprocess the input to produce a preprocessed input include gradient-echo fieldmap data of the rsfMRI data and T1-weighted. The executed instructions may apply the preprocessed input to an AFN model to produce an output, the output including metrics of functional connectivity. The executed instructions may, in response to the output produced by application of the input to the AFN model, determine whether the subject exhibits MS and duration of MS in the subject. The executed instructions may, in response to a determination that the subject exhibits MS, determine a treatment regimen based on the duration of MS in the subject. The executed instructions may transmit the treatment regimen to a user.

In a further embodiment, the metrics of functional connectivity may include model fit statistics and path correlation coefficients. The executed instructions may, prior to producing the output, include preprocessing the input. The executed instructions may apply the preprocessed input to the AFN model.

Other aspects and features of the present disclosure will become apparent to those of ordinary skill in the art after reading the detailed description herein and the accompanying figures.

BRIEF DESCRIPTION OF THE DRAWINGS

The present disclosure can be better understood by referring to the following figures. These drawings illustrate the principles of the disclosure and no limitation of the scope of the disclosure is thereby intended.

FIGS. 3A-3D demonstrate composite SWB co-activation. The SWB AFN map was created by binarizing and spatially adding SWB results of all atrophy seeds. The number of connections to each seed region ranged from 2 to 8. FIGS. 3E-3H demonstrate restriction of SWB co-activation. Whole-brain co-activations were localised to regions of GM atrophy in MS.

Results were overlaid on the Colin27 brain template in Montreal Neurological Institute coordinate space.

Figure 8A:
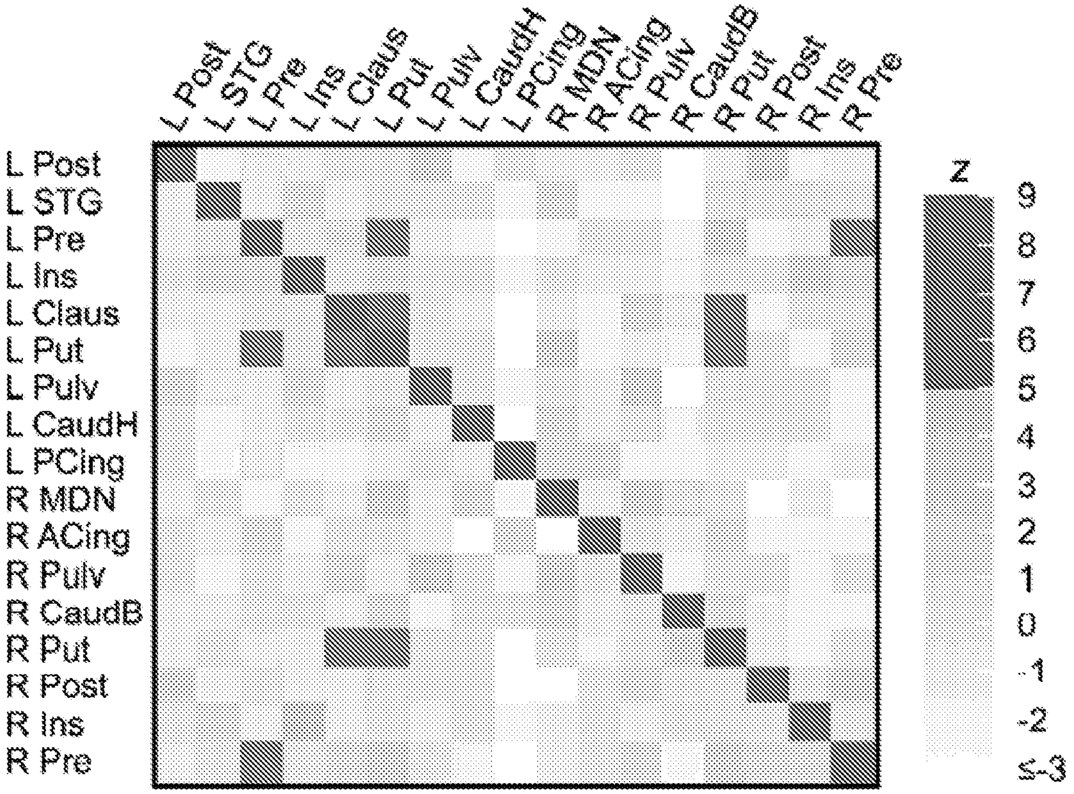
Figure 8B:
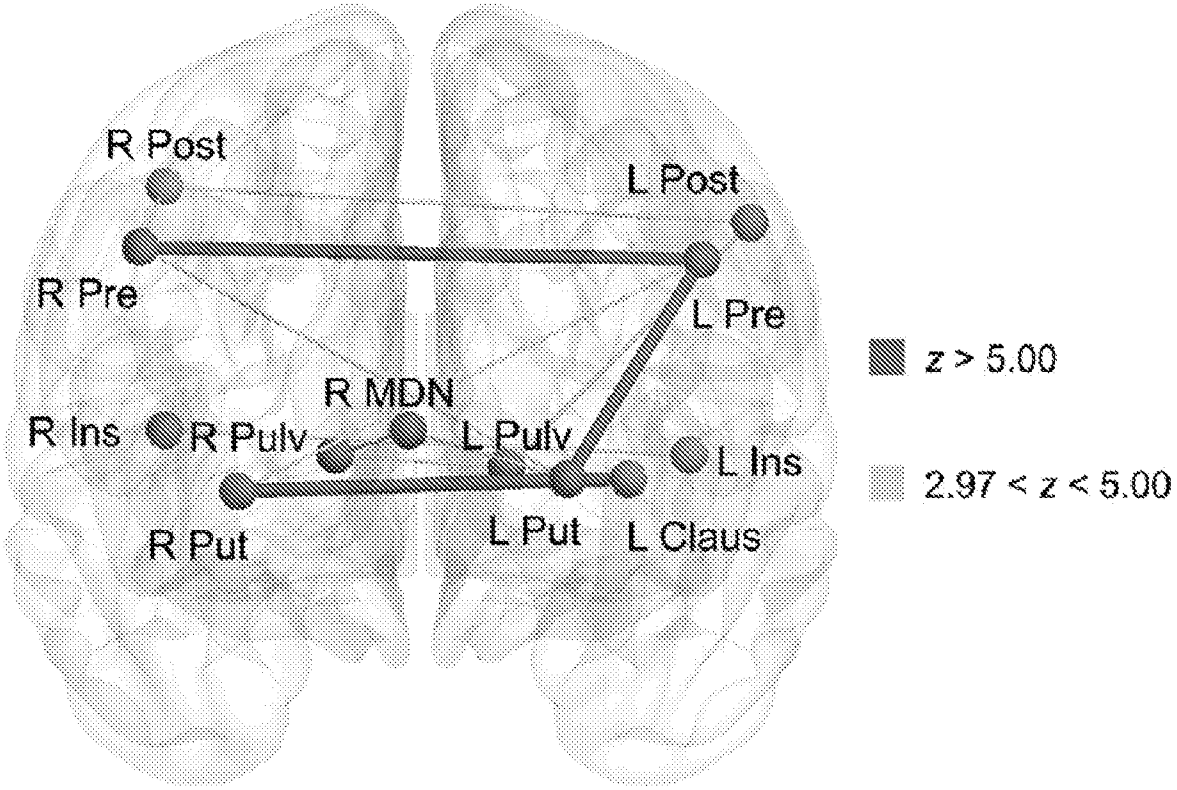

FIG. 8A is a AFN connectivity matrix. FIG. 8B is a AFN node-and-edge model.

Figure 9:
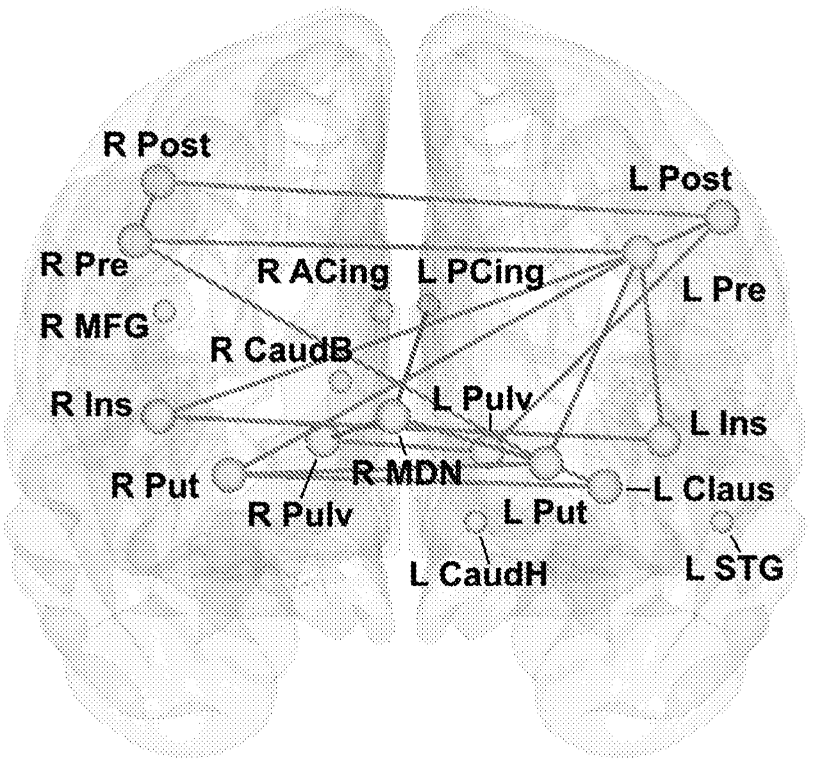

FIG. 9 is a representation of the atrophy-based functional network (AFN) model applied in a prospective resting-state fMRI dataset.

Figure 10:
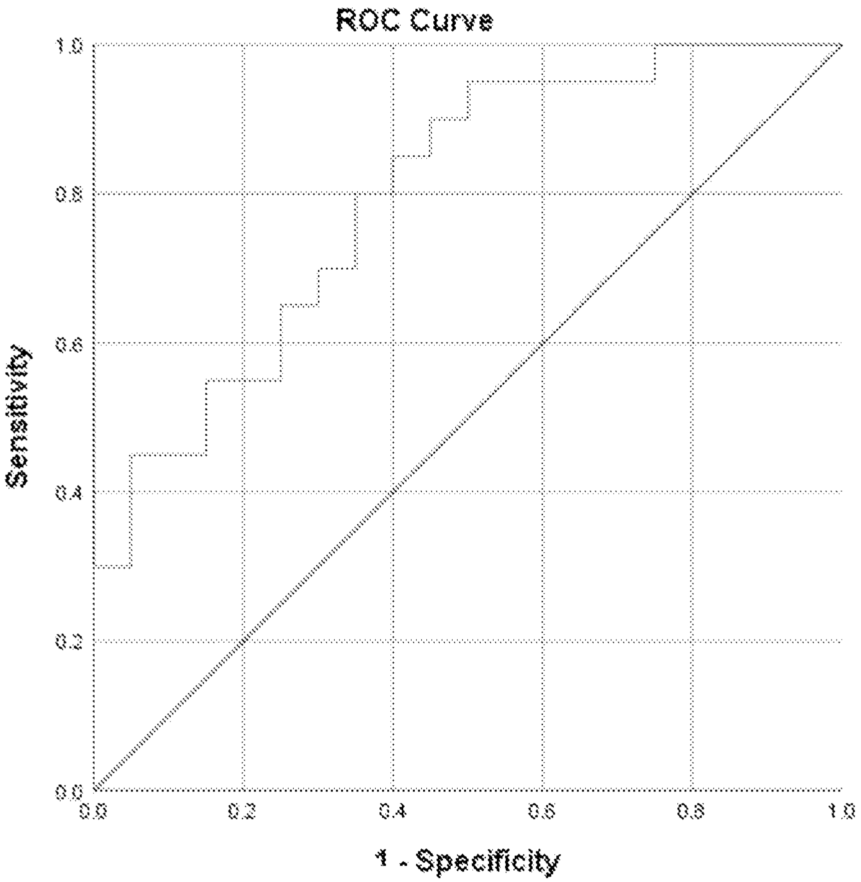

FIG. 10 is a graphical representation of the diagnostic accuracy of the AFN.

Figure 11:
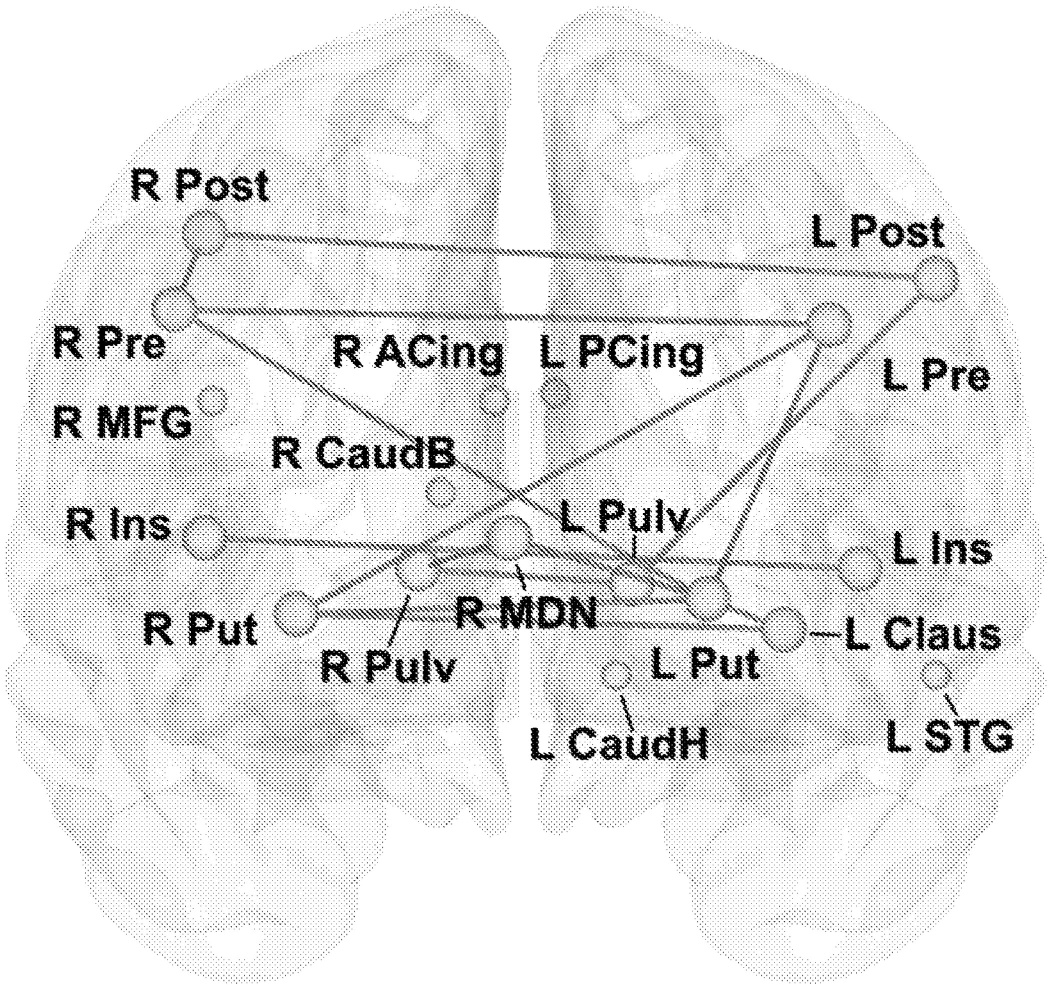

FIG. 11 is an AFN model.

Figure 12A:
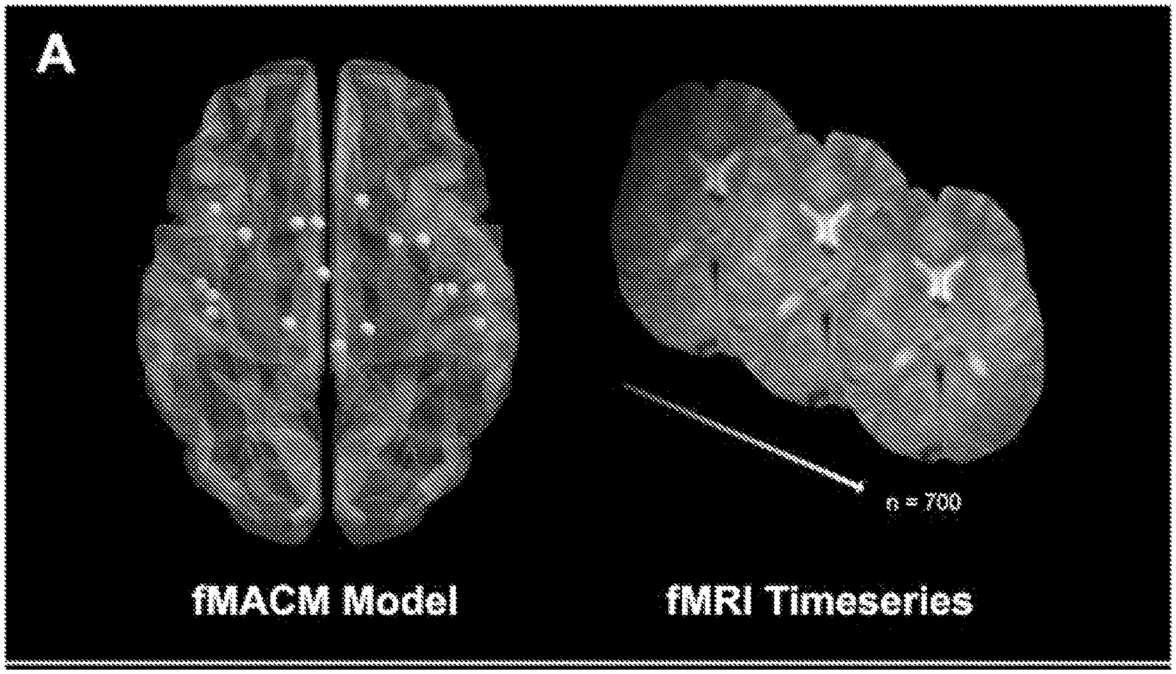

FIG. 12A shows AFN as applied in rsfMRI data to sample the timeseries.

Figure 12B:
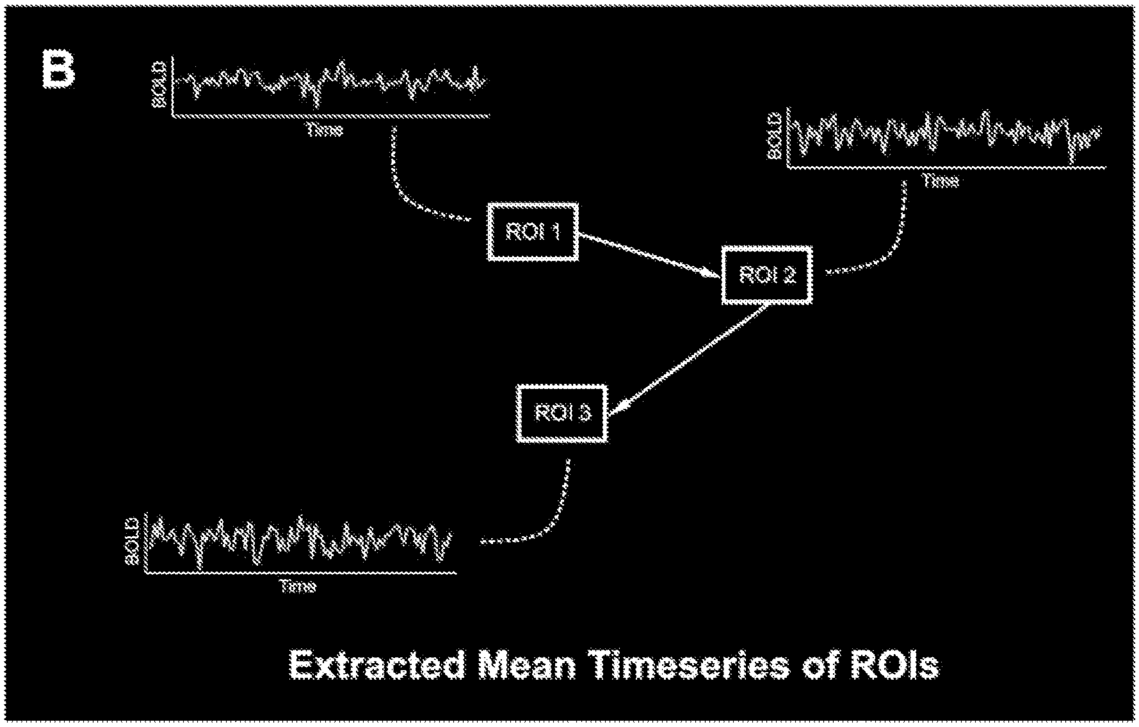

FIG. 12B is a graphical representation of the rsfMRI timeseries that serves as an observed variable in the structural equation modeling path analysis.

Figure 13:
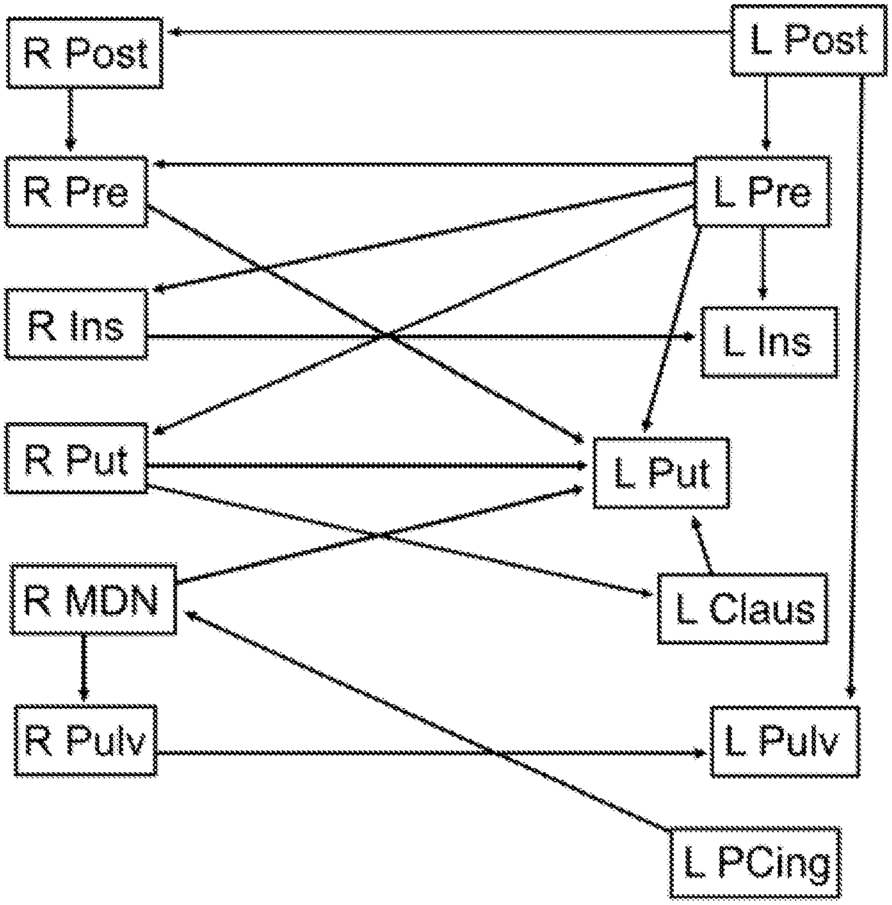

FIG. 13 is a schematic representation of the AFN Applied as a Path Diagram in Structural Equation Modeling (SEM).

Figure 14:
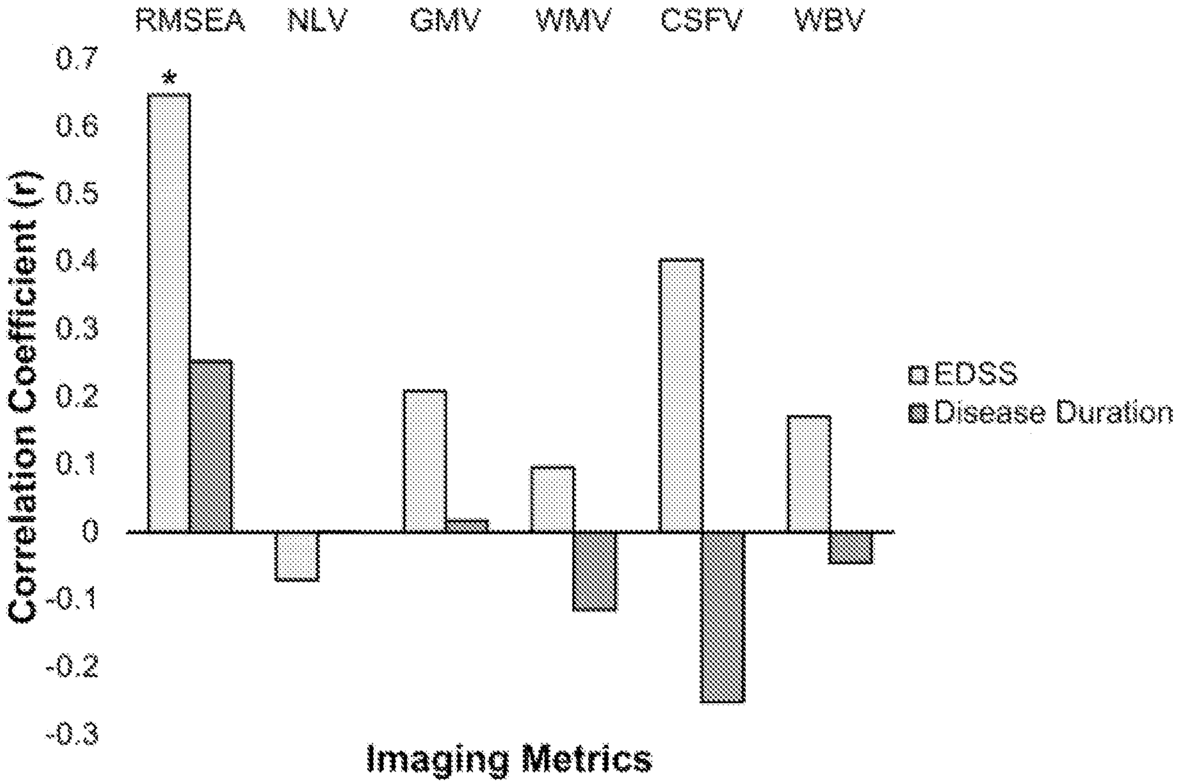
Figure 15A:
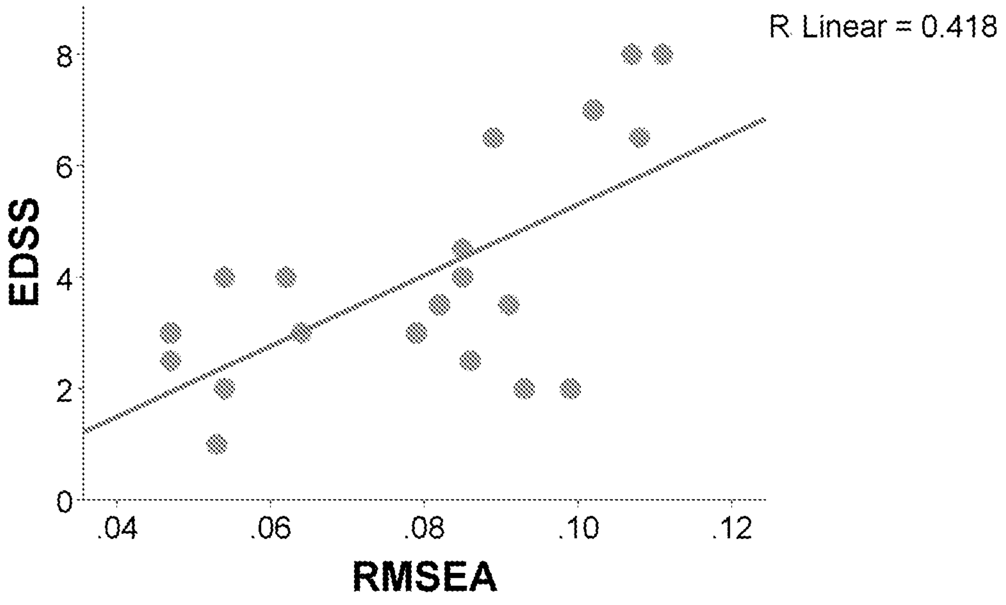
Figure 15B:
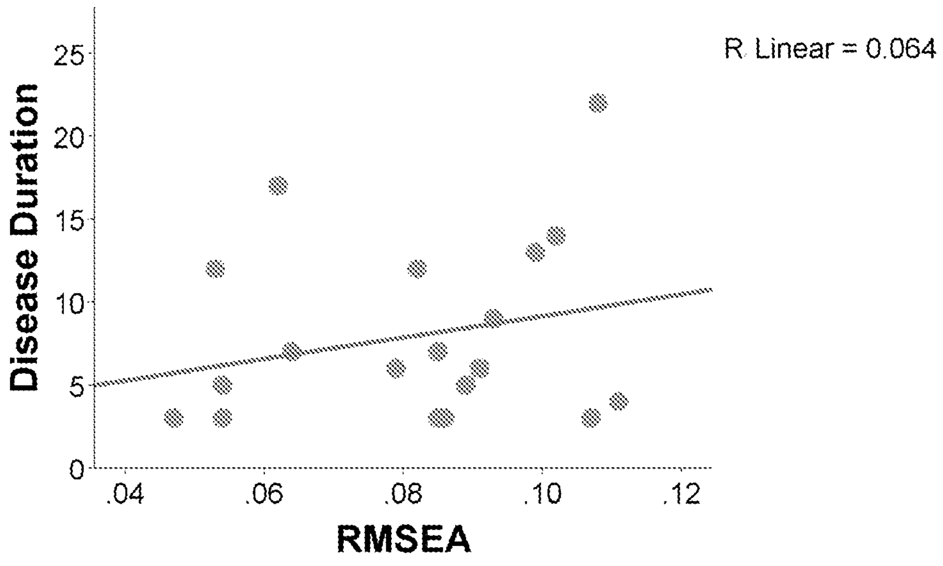
Figure 15C:
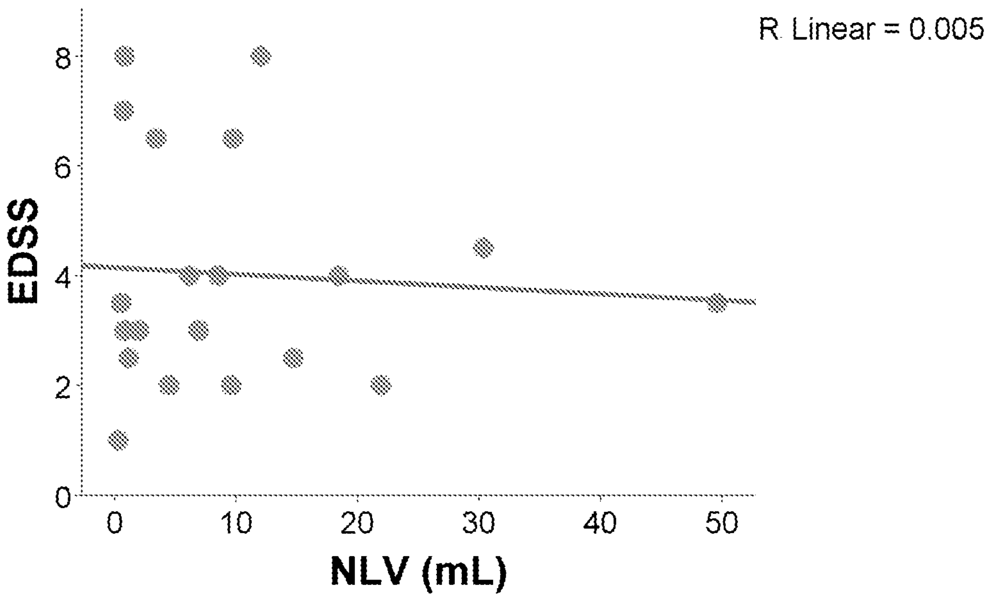
Figure 15D:
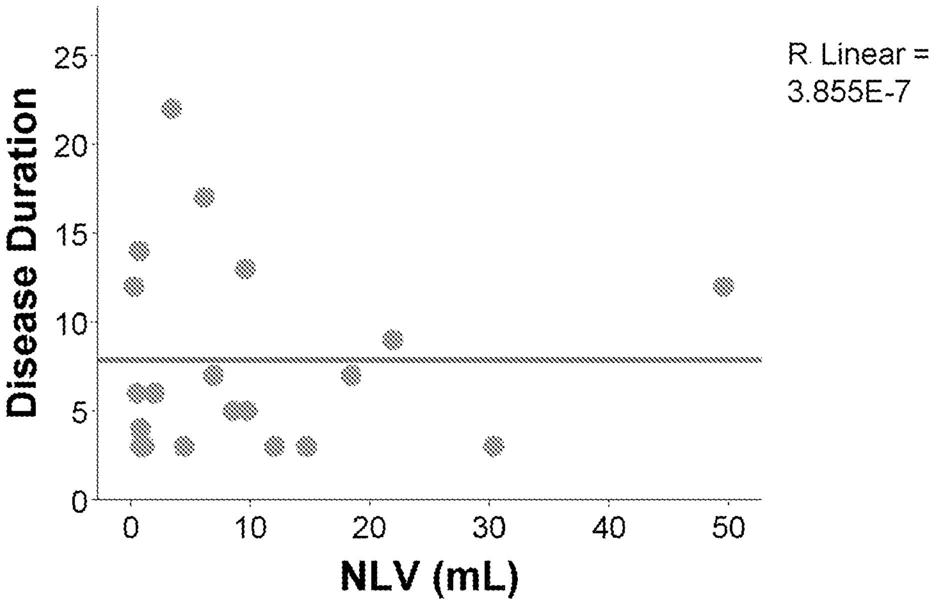

FIG. 14 is a correlation of imaging and clinical characteristics in Multiple Sclerosis.

FIGS. 15A-15D are scatterplots of RMSEA and Disease Burden.

DETAILED DESCRIPTION

Multiple sclerosis is classically described as a demyelinating disease that is characterized by separate attacks, in time and space, on the white matter of the central nervous system (CNS). Currently, clinical MRI methods focus primarily on characterization of demyelinating lesions (e.g. enhancement patterns) for diagnosis, which shows limited correlation with disease progression. However, misdiagnosis of MS remains a challenge with significant clinical and economic consequences. These limitations in patient management have prompted further research to elucidate the pathophysiology of MS. More recently, MS effects have been shown to involve the grey matter and appear to be more widespread than previously thought.

Although inflammation and atrophy have both been found in grey matter to some degree, neurodegeneration has been described as the primary process that is present throughout the disease course. Neurodegeneration is any pathological condition in which neurons lose their function, structure, or both. The distribution of grey matter atrophy in MS has been reported to be focal, involving selective regions, rather than diffuse. There is growing evidence that localized atrophy of subcortical structures demonstrates a strong association with cognitive impairment, more so than white matter lesions load. Additionally, grey matter atrophy involving the sensorimotor cortex has been shown to correlate strongly with clinical disability. However, qualitative evaluation (i.e. visual assessment) for subtle grey matter changes is difficult; and although quantitative neuroimaging methods such as voxel-based morphometry can be used to characterize grey matter atrophy on T1-weighted MRI, this analysis is limited to group-wise testing. On the other hand, functional imaging enables analysis individually. Furthermore, detection of functional abnormalities may be more sensitive than structural abnormalities. Therefore, altered functional connectivity involving localized brain regions prone to exhibiting neurodegeneration serves as a biomarker for early and accurate diagnosis of MS. Provided here are non-invasive methods for detecting altered functional connectivity involving localized brain regions prone to exhibiting neurodegeneration in a subject. This functional network structure (i.e. the atrophy-based functional network (AFN) model) was recently developed for MS. Based on the AFN model, NETFIO-MS was constructed as a medical image analysis tool for application in rsfMRI which enables per-patient quantification of functional network-based disease burden in MS to aid in accurate diagnosis and monitoring of disease progression.

As a medical image analysis tool, NETFIO-MS has the potential to provide per-patient quantitative information on the functional connectivity impairment of the CNS and can aid in the diagnosis and monitoring of MS progression. This new quantitative measurement of neural functional connectivity allows clinicians to more accurately diagnose MS and track disease progression. With this new sensitive tool, doctors can diagnose patients sooner and provide proper treatment earlier to limit disease progression and damage accumulation leading to a better quality of life. Further, this diagnostic algorithm allows clinicians to track patients over time, providing personalized information on disease status and patient responsiveness to different therapeutics, reducing time to effective treatment and reducing overall healthcare burden. The AFN model can guide future development of quantitative neuroimaging markers for diagnosis, evaluating disease progression, and monitoring treatment response.

Validation of NETFIO-MS was completed with a cross-sectional design, involving relapsing-remitting subtype of MS. NETFIO-MS demonstrates discriminant ability between MS and healthy controls; this tool also exhibits utility in monitoring disease progression. However, the AFN model was derived from MS studies of different subtypes. NETFIO-MS is a tool for diagnosing and monitoring MS when applied to a distinct, prospective rsfMRI dataset of MS patients and/or rsfMRI dataset of patients with subtypes of MS, e.g., relapsing-remitting MS.

The functional network structure may be modeled as an AR(1) autoregressive process using structural equation modeling (SEM). This unified SEM approach is taken to improve the temporal representation of rsfMRI, which includes lag variables to correct for the autocorrelations in rsfMRI timeseries data. The observed variables are defined by the mean timeseries data (i.e. AFN nodes). The paths are defined by the functional connectivity between the nodes (i.e. AFN edges). The path analysis computes standardized semi-partial regression coefficients for each AFN edge based on maximum likelihood estimation. The overall model fit statistics are computed to demonstrate the degree of AFN model fit to the rsfMRI. The root mean square error of approximation (RMSEA) is utilized as the primary fit criterion given its relative insensitivity to the effects of sample size; an RMSEA of <0.08 indicates a reasonably good fit to the data.

NETFIO-MS provides path-level and model-level output for diagnosis and monitoring of disease progression, respectively. The path (P) coefficients of P2, P4, P7, P11, and P15 are used for diagnostic purposes. In the validation analysis with age and sex-matched HC, the diagnostic accuracy ranged from acceptable to excellent, AUC=0.805 without incorporation of lag variables and AUC=0.798 with incorporation of lag variables. The model fit statistic of RMSEA tracks disease progression. In the validation analysis, the RMSEA correlated strongly with the Expanded Disability Status Scale (EDSS) score (r=0.66) and moderately with disease duration (r=0.32), corrected for number of years of education. As a comparison, the normalized lesion volume (NLV) of white matter hyperintensities on T2-weighted FLAIR images correlated weakly with both EDSS (r=−0.19) and disease duration (r=0.15).

Current clinical magnetic resonance imaging (MRI) methods focus primarily on the enhancement patterns of demyelinating lesions for diagnosis, which show limited correlation with disease progression. Additionally, treatment with immunomodulatory therapy has been found to be partly effective in early MS but inadequate in managing the spectrum of disease subtypes. These limitations in patient management have prompted further research to elucidate the pathophysiology of MS. More recently, MS effects have been shown to involve the grey matter (GM) and appear to be more widespread than previously thought. The distribution of GM atrophy in MS has been reported to be focal, involving selective regions, rather than diffuse. There is growing evidence that localized atrophy of subcortical structures demonstrates a strong association with cognitive impairment, more so than the WM lesion load. Additionally, GM atrophy involving the sensori-motor cortex has been shown to correlate strongly with clinical disability. Given the difficulty of visualizing subtle GM changes, quantitative neuroimaging methods such as voxel-based morphometry (VBM) can be used to characterize GM atrophy on T1-weighted MRI; this analysis, however, is limited to group-wise testing. On the other hand, functional imaging enables analysis at the per-subject level. Furthermore, detection of functional abnormalities may be more sensitive than structural abnormalities.

Functional network abnormalities have been described in several neurodegenerative disorders. Additionally, brain regions that are selectively vulnerable to GM atrophy have been shown to act as "nodes" in functional networks; this forms the basis for the network degeneration hypothesis (NDH). One could then consider the regions affected by GM atrophy as a network and assess the functional relationship between these regions (i.e., functional connectivity). In MS, functional network abnormalities have been demonstrated, but the heterogeneity of study designs and findings necessarily limit their generalisability. Therefore, to test the NDH in MS, there is a need to determine convergent structural and functional changes by: (1) defining localised regions of GM atrophy and (2) creating a functional connectivity model based on these GM regions. To this end, the BrainMap neuroimaging database was used to perform structure-based functional connectivity modeling meta-analytically.

Coordinate-based-meta-analysis (CBMA) using BrainMap is a powerful method used to quantify consistent structural brain alterations and determine associated functional network involvement without laboratory bias. The BrainMap environment includes published coordinate-based results data standardized using an x-y-z mapping system of the brain. There are two domains in the database: functional (3,261 publications, 16,158 experiments, 125,588 coordinates, 72,299 patients) and structural (994 publications, 3,151 experiments, 125,588 coordinates, 72,299 patients). This large-scale, data-driven approach mitigates against the limitations faced by individual primary studies with relatively restricted sample sizes. Additionally, CBMA uses data-reduction to circumvent the issue of heterogeneity in the literature. This is accomplished by applying the anatomical likelihood estimation (ALE) algorithm to BrainMap data, which provides statistical rigor in computing significant convergence of neuroimaging results. ALE first estimates the spatial uncertainty (probability distribution) of each point in coordinate-based data by accounting for inter-subject and inter-laboratory variability typically observed in individual experiments. Then, the algorithm computes the union of spatial probabilities for each voxel and calculates the above-chance clustering of results between experiments (i.e., random-effects analysis). Subsequently, the structural results from ALE can be used in AFN modeling to determine inter-regional co-activation, which is a surrogate for functional connectivity. AFN results are comparable to functional connectivity analyses in healthy controls and have been validated using resting-state functional MRI (rsfMRI). Thus, the disease-specific functional network model derived from this study can be applied directly in primary rsfMRI data to characterize functional connectivity abnormalities in MS patients.

The embodiments or examples disclosed herein may include training and/or utilization of a meta-analytical model and/or a machine learning model to diagnose and/or determine a treatment regimen for varying stages of MS. Further, the meta-analytical model and/or machine learning model may provide for monitoring and assessment of MS in response to a specific treatment. Systems and methods described herein provide decision support tools for healthcare professionals when they are evaluating treatment regimens with and for a specific patient. Treatment regimens may be disease modifying therapies or symptom management therapies. Certain treatment regimens may be provided to prevent the relapses due to MS. Certain treatment regimens may be designed to decrease long-term disability and/or improve the symptoms due to MS. Certain treatment regimens may prevent changes in memory and other brain function due to MS. Certain treatment regimens may target the changes in specific regions of the brain as seen on MRI due to MS. These treatment regimens have to evaluated for suitability to a specific patient. Suitable treatment regimens may include one or more pharmaceutical products, such as interferon beta medications, azathioprine, glatiramer acetate, cyclophosphamide, fingolimod, dimethyl fumarate, mitoxantrone, mycophenolate mofetil, diroximel fumarate, teriflunomide, siponimod, and cladribine. Suitable treatment regimens may include one or more biologics, such as ocrelizumab, natalizumab, rituximab, and alemtuzumab.

Certain treatment regimens may include pharmaceutical products to manage side effects and symptoms, such as muscle relaxants (e.g. baclofen, tizanidine, cyclobenzaprine, or onabotulinum toxin) and other medications to reduce fatigue, depression, or pain.

EXAMPLES

It should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples and are not for the purpose of limitation thereof. Also, it will be appreciated that one or more of the following-described aspects, expressions of aspects, and/or examples, can be combined with any one or more of the other following-described aspects, expressions of aspects and/or examples. Certain exemplary aspects will now be described to provide an overall understanding of the principles of the structure, function, manufacture, and use of the systems and methods disclosed herein. One or more examples of these aspects are illustrated in the accompanying drawings.

Example 1

Systems and Methods

Figure 1:
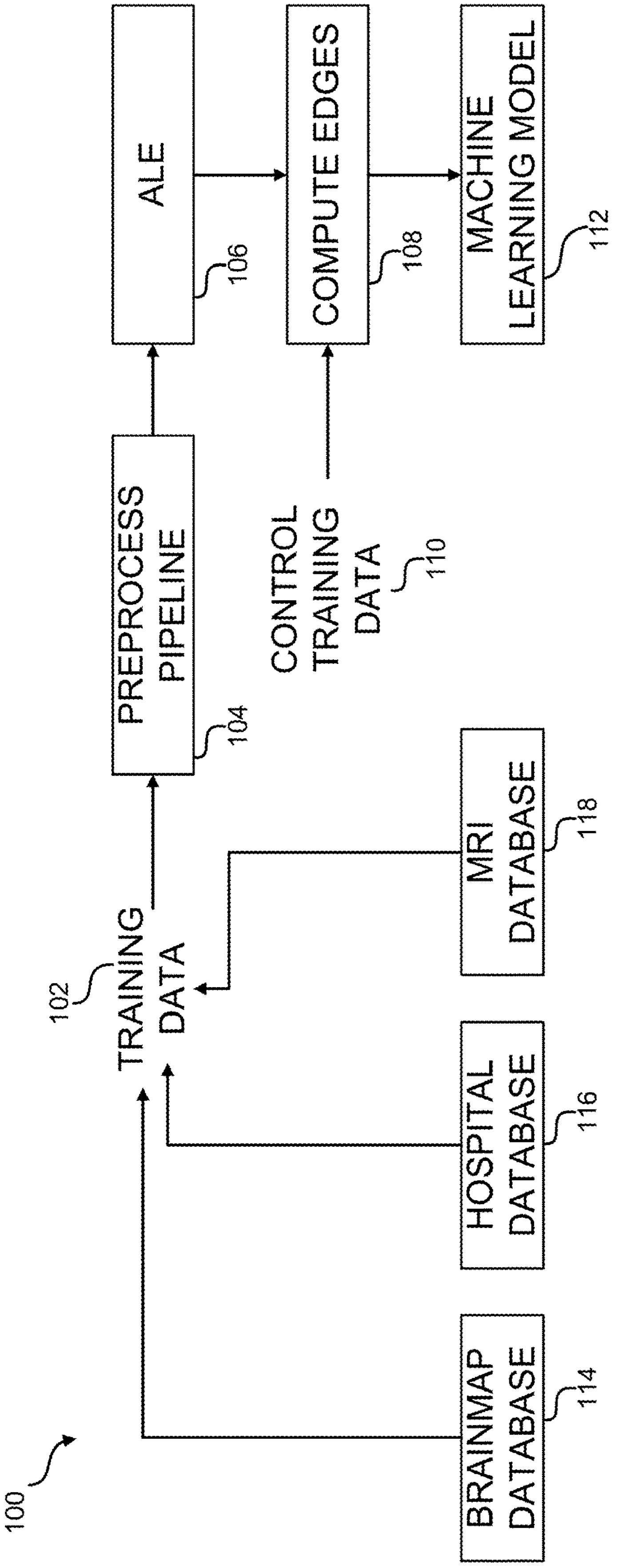
FIG. 1 is a block diagram of a system to train an atrophy-based functional network (AFN) model, according to an embodiment of the present disclosure.

A system to train or generate the AFN model or classifier (e.g., a meta-analytical model, trained machine learning model, and/or other classifier to accept an input and produce an output), is illustrated in FIG. 1. The system 100 may accept or receive data from various databases as training data 102. Databases providing training data 102 may include the BrainMap neuroimaging database 114 (as described herein), a hospital database 116, a MRI database 118, and/or other databases including rsfMRI data. The data may be received or provided directly from the databases or via a client or user interface.

The training data 102 may include a number of subjects rsfMRI data. Each subject may have a known diagnosis and/or degree or progression of MS. Each subject's diagnosis may be indicated by a value. The value may be a number or text indicating whether the subject has MS and, if so, the severity, progression, or degree of MS the subject is exhibiting. Other data may be included in the training data, such as clinical data and/or other types of MRI data. Further, the training data may include data for a number of subjects, e.g., 100 subjects, 500 subjects, 1000 subjects, 10,000 subjects, and more.

After reception of the training data 102 at the system 100, the training data 102 may be transmitted to a preprocess pipeline 104. The preprocess pipeline 104 may, for each set of images, video, or animation of a rsfMRI, perform linear and nonlinear image registration, motion correction, field-map unwarping, slice timing correction, spatial smoothing, temporal filtering, noise reduction (in addition to any noise reduction already performed), or some combination thereof. Other image preprocessing may be performed. In an embodiment, the preprocess pipeline 104 may produce, for each image, a preprocessed input or preprocessed set of training data. Such an input may include gradient-echo fieldmap data of the rsfMRI data and/or T1-weighted data.

After the training data 102 is preprocessed in the preprocess pipeline 104, the preprocessed training data may be transmitted to an Anatomical likelihood estimation (ALE) module 106 to determine a consistent pattern of GM atrophy in MS (as described below). In another embodiment, rather than determining the pattern of GM atrophy in MS, such a pattern may be a predetermined input utilized to train the AFN model or classifier.

After the pattern of GM atrophy is determined (e.g., at ALE module 106) or input, the training data may be transmitted a module to compute edges 108. As a separate input, additional control training data 110 may be input at this point. Such control training data 110 may include healthy rsfMRI data (e.g., patients not diagnosed with and/or not exhibiting MS) and/or other data, similar to the data provided for training data 102. In another example, the control training data 110 may be input with the training data 102. In such examples, all data input as training data 102, as noted above, may include an indicator to indicate whether a particular rsfMRI scan or data is of a subject with or without MS. The indicator may be a bit (e.g., 1 or 0 to indicate no MS or MS diagnoses), text (e.g., yes or no), a number, or some other value to indicate whether a patient or subject has been diagnosed with MS and the severity or progression of MS in the patient or subject. The module to compute edges 108 may assess inter-regional functional connectivity and/or define edges between specified nodes. Similar to the pattern of GM atrophy in MS, edges may be predefined prior to training the AFN model or classifier and the edges may be provided as an input.

Once the training data 102 has been preprocessed, the pattern of GM atrophy in MS determined or input, and/or the edges between specific nodes determined or input, the input or training data may be transmitted to a machine learning model 112 or a meta-analytical model. The input to the machine learning model 112 or a meta-analytical model may include the training data (e.g., control or healthy subject data and data of subjects with MS of varying degrees), the pattern of GM atrophy in MS, the edges between specified nodes, and/or other data. The other data which may be included in the input per subject, such as clinical data. Clinical data may include various patient or subject data, such as age, height, weight, sex, race, ethnicity, family history of MS diagnosis, and/or other data. The machine learning model may be trained such that a trained machine learning model, classifier, predictor, and/or probability is produced. Various machine learning models may be utilized to create the trained machine learning model, classifier, predictor, and/or probability of MS diagnoses and/or a degree or progression of MS in a patient, based on the input described above. Models and methods may include decision trees, random forest models, random forests utilizing bagging or boosting (as in, gradient boosting), neural network methods, support vector machines (SVM), other supervised learning models, other semi-supervised learning models, other unsupervised learning models, or some combination thereof, as will be readily understood by one having ordinary skill in the art. Other types of models may be utilized to produce a diagnostic and treatment tool, such as the meta-analytical model or another statistical or probabilistic model.

Figure 2:
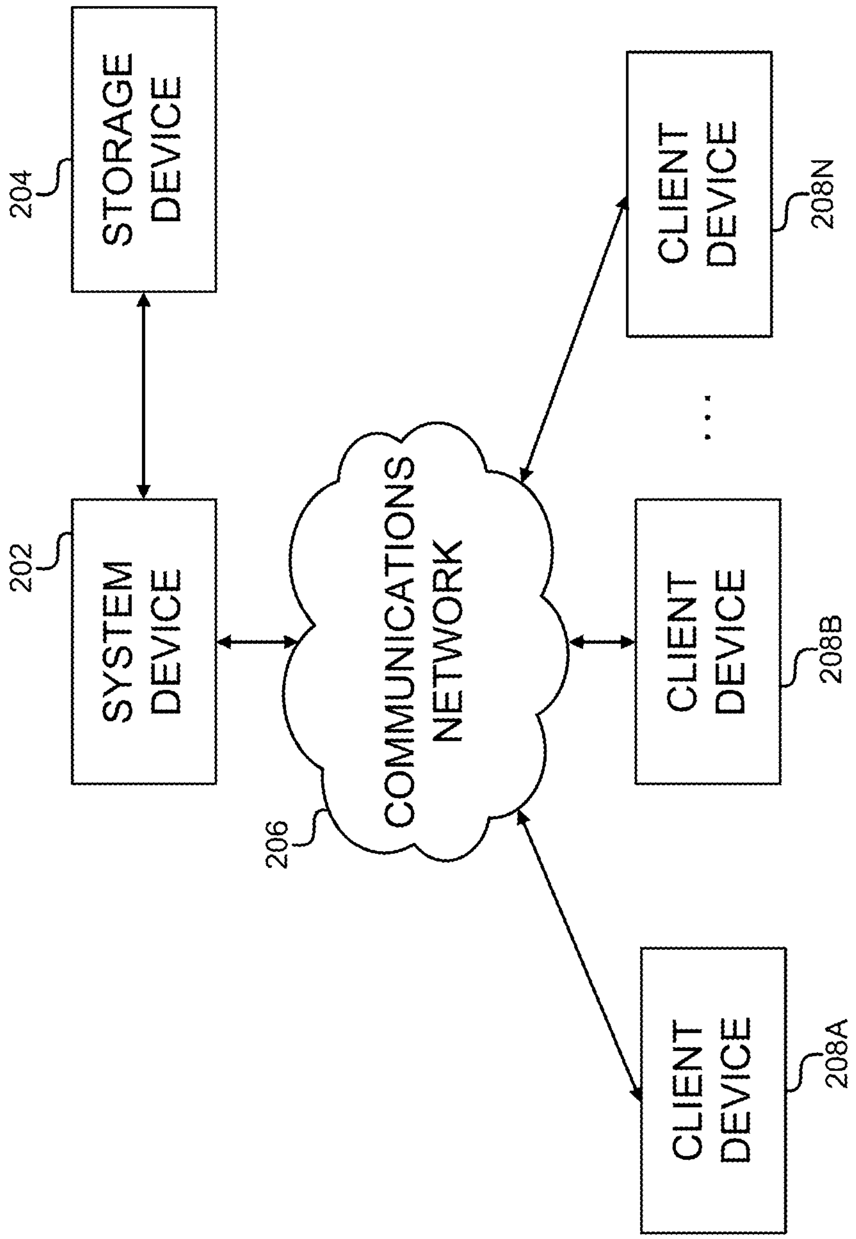
FIG. 2 is a block diagram in which some example embodiments may be used for generating and/or utilizing an atrophy-based functional network (AFN) model.
Figure 3:
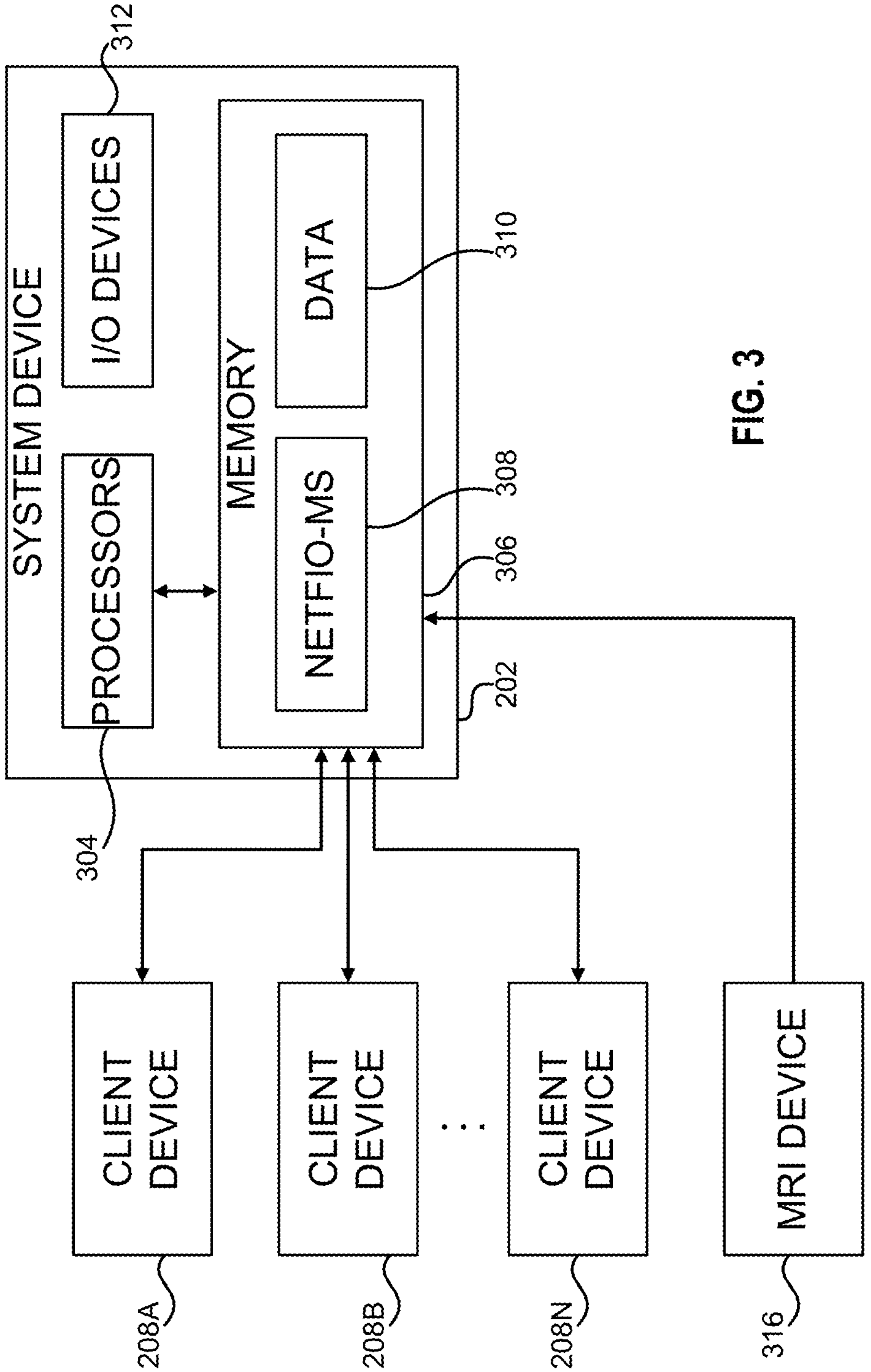
FIG. 3 is a block diagram of a system to utilize an atrophy-based functional network (AFN) model.
Figure 4:
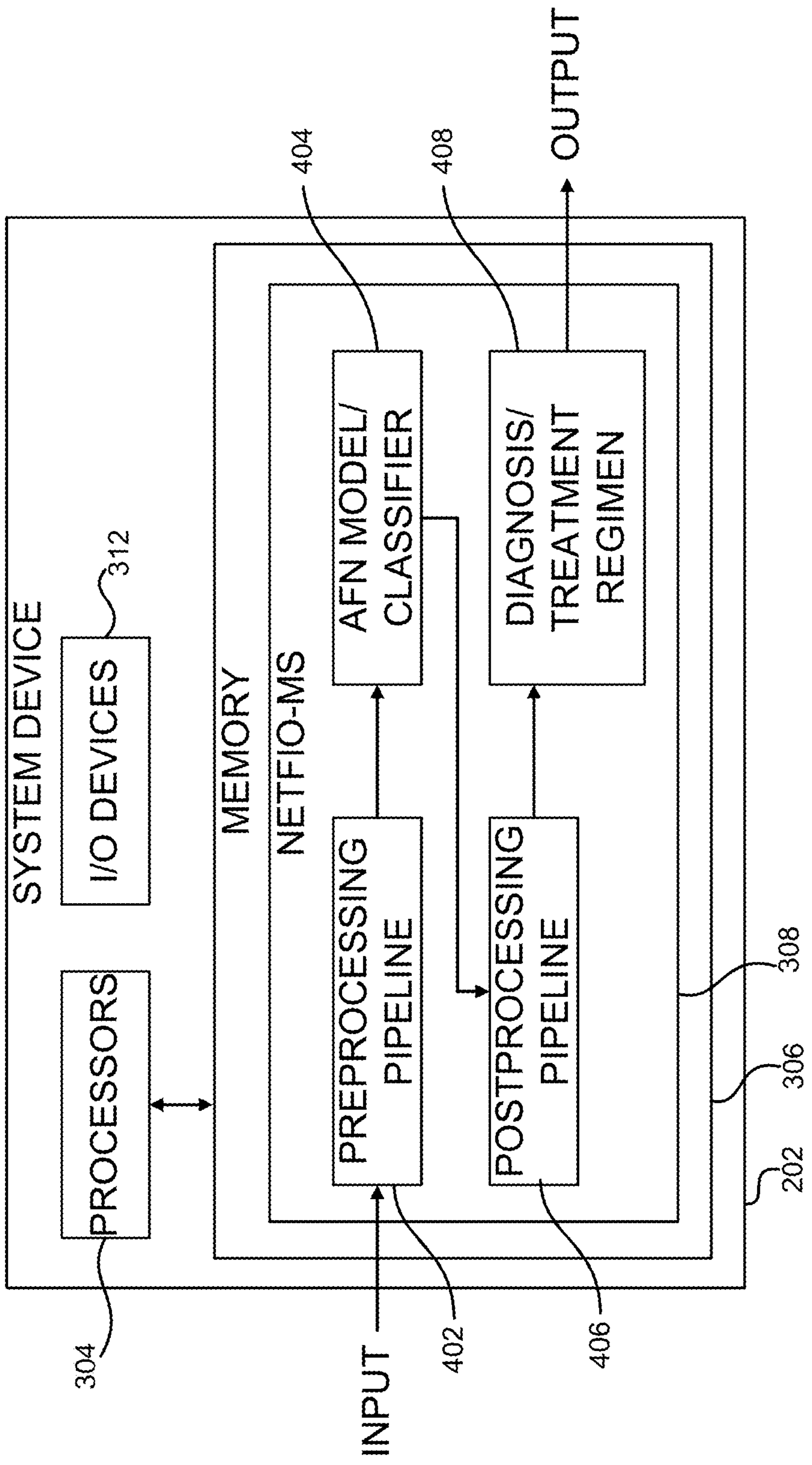
FIG. 4 is another block diagram of a system to utilize an atrophy-based functional network (AFN) model.

FIG. 2 is a block diagram in which some example embodiments may be used for generating and/or utilizing an atrophy-based functional network (AFN) model. FIG. 2 illustrates an example environment within which embodiments of the present disclosure may operate. As illustrated, a system device 202 is shown that may perform various operations for generating and/or utilizing an atrophy-based functional network (AFN) model, in accordance with the embodiments set forth herein. The system device 202 is connected to a storage device 204. Although system device 202 and storage device 204 are described in singular form, some embodiments may utilize more than one system device 202 or one or more storage device 204. The system device 202 and any constituent components (e.g., processors 304, memory 306, I/O devices 312, and/or instructions stored in the memory as illustrated in FIGS. 3-4) may receive and/or transmit information via communications network 206 (e.g., the Internet, direct or hardwired connection, local networks, cloud based networks, and/or other wireless connections) with any number of other devices. In this regard, system device 202 may be implemented as one or more servers or other computing devices that may interact via communications network 206 with one or more client devices, shown in FIG. 2 as client device 208A, client device 208B, through client device 208N. In this way, the system device 202 may interact with a number of users by offering the ability to utilize the AFN model in a software-as-a-service (SaaS) implementation or allow a specified user to generate the AFN model. System device 202 may alternatively be implemented as a device with which users may interact directly (e.g., a laptop, desktop, tablet, or other computing device). In such embodiments, a user may utilize the system device 202 directly to generate and/or use the AFN model.

System device 202 may be entirely located at a single facility such that all components of system device 202 are physically proximate to each other. However, in some embodiments, some components of system device 202 may not be physically proximate to the other components of system device 202, and instead may be connected via communications network 206.

Storage device 204 may comprise a distinct component from system device 202, or it may comprise an element of system device 202 (e.g., memory 306, as described below in connection with FIG. 3). Storage device 204 may be embodied as one or more direct-attached storage (DAS) devices (such as hard drives, solid-state drives, optical disc drives, or the like) or may alternatively comprise one or more databases or Network Attached Storage (NAS) devices independently connected to a communications network (e.g., communications network 206). Storage device 204 may host the software and/or algorithms executed to operate the system device 202 to generate or utilize the AFN model. In addition, or in the alternative, storage device 204 may store information relied upon during operation of the system device 202, such as training data or a data set used for generation of a given AFN model. In addition, storage device 204 may store control signals, device characteristics, and access credentials enabling interaction between the system device 202 and one or more of client device 208A through client device 208N.

Client device 208A through client device 208N may be embodied by any computing devices known in the art, such as desktop or laptop computers, tablet devices, smartphones, or the like. These devices may be independent devices, or may, in some embodiments, be peripheral devices communicatively coupled to other computing devices. Although FIG. 2 illustrates an environment and implementation of the present disclosure in which the system device 202 interacts with one or more of client device 208A through client device 208N, in some embodiments clients may directly interact with the system device 202 (e.g., via input/output circuitry of system device 202), in which case a separate client device need not be utilized. Whether by way of direct interaction or via a separate client device, a client may communicate or otherwise interact with the system device 202 to perform functions described herein and/or achieve benefits as set forth in this disclosure.

As illustrated in FIGS. 3 and 4, the system device 202 may include processors 304, I/O devices 312 (to provide communication with client devices and/or other devices), and memory 306. The processors 304, processing resource, or processing circuitry may be a plurality of processors connected together in communication with an electronic communications network. In other embodiments, the processors 304 may be a group of graphical processing units configured to work in parallel as a GPU cluster. A processor may include a single processor device and/or a plurality of processor devices (e.g., distributed processors). Processors 304 may be any suitable processor capable of executing/performing instructions. Processors 304 may include a central processing unit (CPU) that carries out program instructions to perform the basic arithmetical, logical, and input/output operations required to execute the method of predicting MS or degree or progression of MS in a patient and/or for providing decision support to healthcare professionals to implement a treatment regimen for a patient already diagnosed with MS. A processor 304 may include code (e.g., processor firmware, a protocol stack, a database management system, an operating system, or a combination thereof) that creates an execution environment for program instructions. Processes and logic flows described herein may be performed by one or more programmable processors executing one or more computer programs to perform functions by operating on input data and generating corresponding output.

The memory 306 may be a non-transitory machine-readable storage medium. A machine-readable storage medium may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (e.g., hard drive), a solid state drive, any type of storage disc, and the like, or a combination thereof. As noted, the machine readable storage medium may store or include instructions executable by the processors 304.

In an embodiment, the generated AFN model or classifier (as described above) may be stored in memory 306 of the system device 202. The system device 202 may also include data 310 or other instructions for utilization of the AFN model. In such embodiments, the system device 202 may include the NETFIO-MS 308, which may include the AFN model or classifier, among other instructions (e.g., pre and post processing, diagnosis, and/or treatment regimen generation) executable by the processors 304.

In such embodiments, the system device 202 may receive a rsfMRI from client device 208A through client device 208N, from a MRI device 316, and/or from another source or database via I/O devices 312. As the input is received, the system device 202 may transmit the input to a preprocessing pipeline 402 of the NETFIO-MS 308. The preprocessing pipeline 402 may preprocess the data, e.g., reduce noise, perform linear and nonlinear registration, perform motion correction, perform fieldmap unwarping, perform slice timing correction, perform spatial smoothing, perform temporal filtering, and/or weight different data points as determined via training. As noted, the input may include the rsfMRI and may additionally include clinical data.

After preprocessing the input, the preprocessing pipeline 402 may provide a preprocessed input (e.g., the preprocessed rsfMRI, a gradient-echo fieldmap data of the rsfMRI data, and/or T1-weighted data) to the AFN model or classifier 404 (e.g., the trained machine model, met-analytical model, statistical model, or probabilistic model). In other words, the preprocessed input may be applied to the AFN model or classifier 404. Such an application may produce an output, such as a value, predictor, or probability. For example, the value may be a number between 1 and 0. Different thresholds may indicate severity of MS (high to none) or simply whether the patient may have MS or not. In another embodiment, the output may be a set of indices, e.g., edge weights, model fit statistics, and/or images of the patient's brain with areas of importance highlighted. Such an output may be transmitted to a post processing pipeline 406. The post processing pipeline 406 may add clinical predictors, adjust edge weights, and/or set an adjusted threshold.

The output and/or post processed output may be transmitted to a diagnosis and/or treatment regimen module 408. Based on the output and/or post processed output, the diagnosis and/or treatment regimen module 408 may offer a diagnosis of a patient and/or a treatment regimen (e.g., medication to be taken or other types of treatments). The final diagnosis and/or treatment regimen may be transmitted to a client device (e.g., client device 208A through client device 208N), a user interface of the client device, to storage device 204, to another user or storage location, or some combination thereof.

Figure 5:
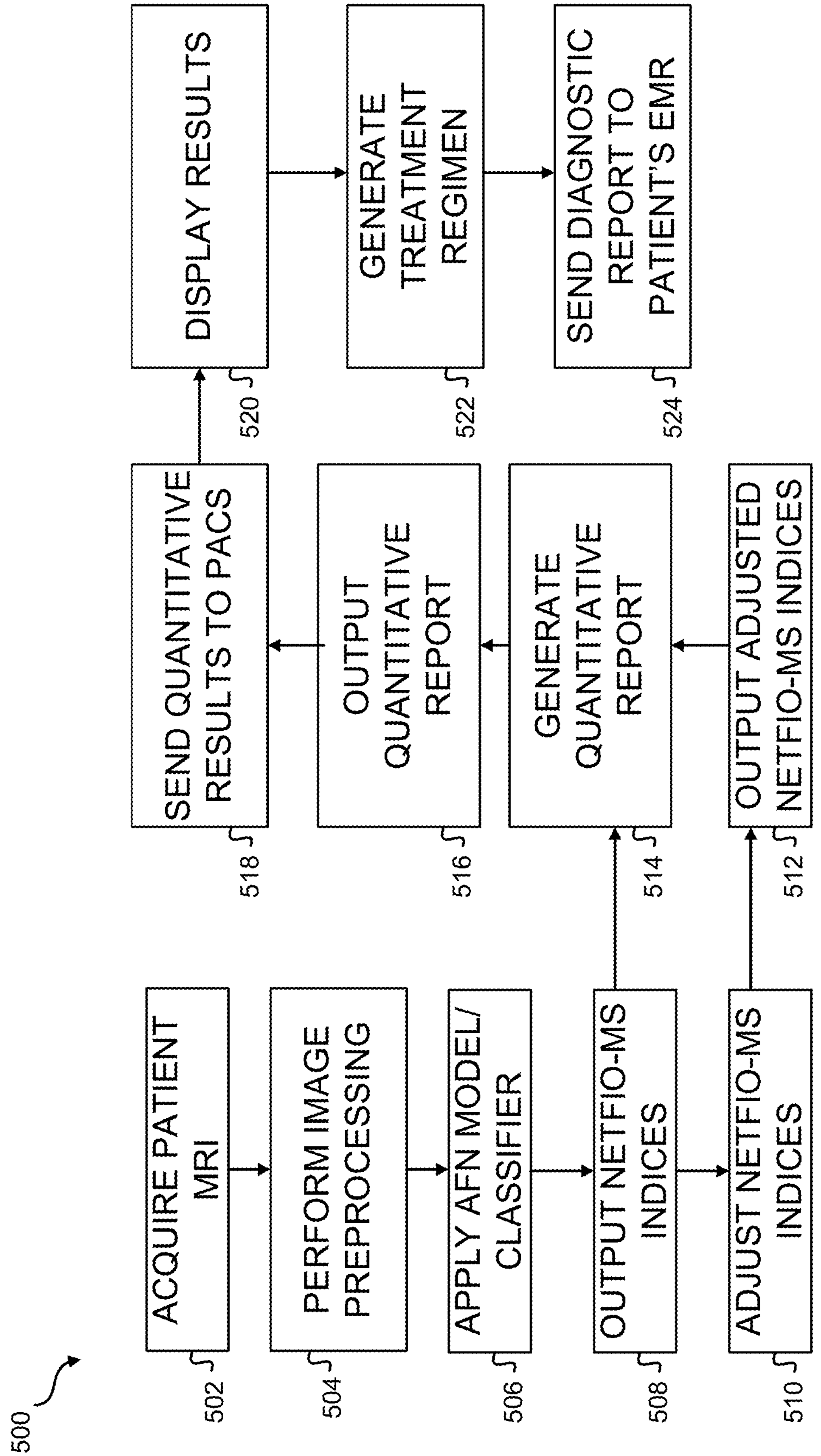
FIG. 5 is a flowchart of a method to utilize an atrophy-based functional network (AFN) model, according to an embodiment of the present disclosure.

FIG. 5 illustrates flow diagrams, implemented in a system or computing device, to predict or diagnose whether a subject or patient has MS and/or the progression, severity, or degree to which the subject or patient exhibits MS, according to an embodiment. The method is detailed with reference to the system device 202. Unless otherwise specified, the actions of method 500 may be completed within the system device 202. Specifically, method 500 may be included in one or more programs, protocols, or instructions loaded into the memory 306 of the system device 202 and executed on the processor or one or more processors 304 of the system device 202. The order in which the operations are described is not intended to be construed as a limitation, and any number of the described blocks may be combined in any order and/or in parallel to implement the methods.

At block 502, the system device 202 may acquire or receive a rsfMRI. The system device 202 may acquire the patient's rsfMRI from a client device (e.g., client device 208A through client device 208N), an MRI device 316, a database, storage device 204, or other source or location. In another embodiment, the system device 202 may receive the rsfMRI, a gradient-echo fieldmap data of the rsfMRI data, T1-weighted data, the patient's clinical data, or some combination thereof.

At block 504, the system device 202 may perform image preprocessing, e.g., via preprocessing pipeline 402. The preprocessing pipeline 402 may reduce noise, perform linear and nonlinear registration, perform motion correction, perform fieldmap unwarping, perform slice timing correction, perform spatial smoothing, perform temporal filtering, and/or adjust weight of different data points.

After preprocessing, the preprocessed data may be transferred and/or applied to the AFN model or classifier 404. As noted, when the processed input is applied to the AFN model or classifier 404, a value is produced. Such a value may indicate whether the patient is to be diagnosed with MS and to what degree. Other values may be output, at block 508, such as indices, e.g., edge weights, model fit statistics, and/or the set or preset diagnostic thresholds.

At block 510, the indices may be adjusted, based on clinical predictors, computed and adjusted edge weights, and adjusted diagnostic thresholds. The adjusted indices may be, at block 512, transferred as an output for reporting.

At block 514, the system device 202 may, based on the output indices and adjusted indices, generate a quantitative diagnosis report for the patient. The quantitative diagnostic report may include whether the patient has MS and, if so, the progression or degree of MS. Further, if the patient has been on a treatment regimen, the report may include the last report for the patient, if available from a medical records database or in the patient's electronic medical records (EMR). Further, the report may include information on the last treatment regimen and if the treatment regimen has affected the progression or degree of MS in the patient. In other words, the effectiveness of a particular treatment regimen may be determined.

At block 516, the report may be transmitted as an output. The report, at block 518, may be stored at a picture archiving and communication system (PACS). The report may then be transmitted and displayed to a clinician or doctor, at block 520. In an embodiment, the output may include the diagnosis of the patient, an image illustrating the patient's brain with edges and connections between them, regression or progression since a last report for patients already diagnosed with MS, a determination on treatment effectiveness, a treatment regimen, and/or an update to a patient's existing treatment regimen.

In an embodiment, the report may or may not include a treatment regimen. In another embodiment, a clinician or doctor may decide, at block 522, to generate the treatment regimen after viewing the report. In such embodiments, the clinician or doctor may select an option at the client device to generate the treatment regimen, which will then be displayed to the clinician or doctor. At block 524, the report and/or treatment regimen may be transmitted and stored in the patient's EMR.

Example 2

Materials and Methods

The study protocol adhered to standard quality criteria of BrainMap CBMA, which is based on the BrainMap metadata coding scheme. This study was also compliant with the Preferred Reporting Items for Systematic Reviews and Meta-analyses statement. In other embodiments, additional data, gathered, for example, from a hospital database, medical record database, a MRI database, and/or any other source of data including rsfMRI data of patients with a known diagnosis (e.g., a patient exhibiting a specific stage or progression of MS or a patient not exhibiting MS).

Figures 6A, 6B, 6C, 6D:
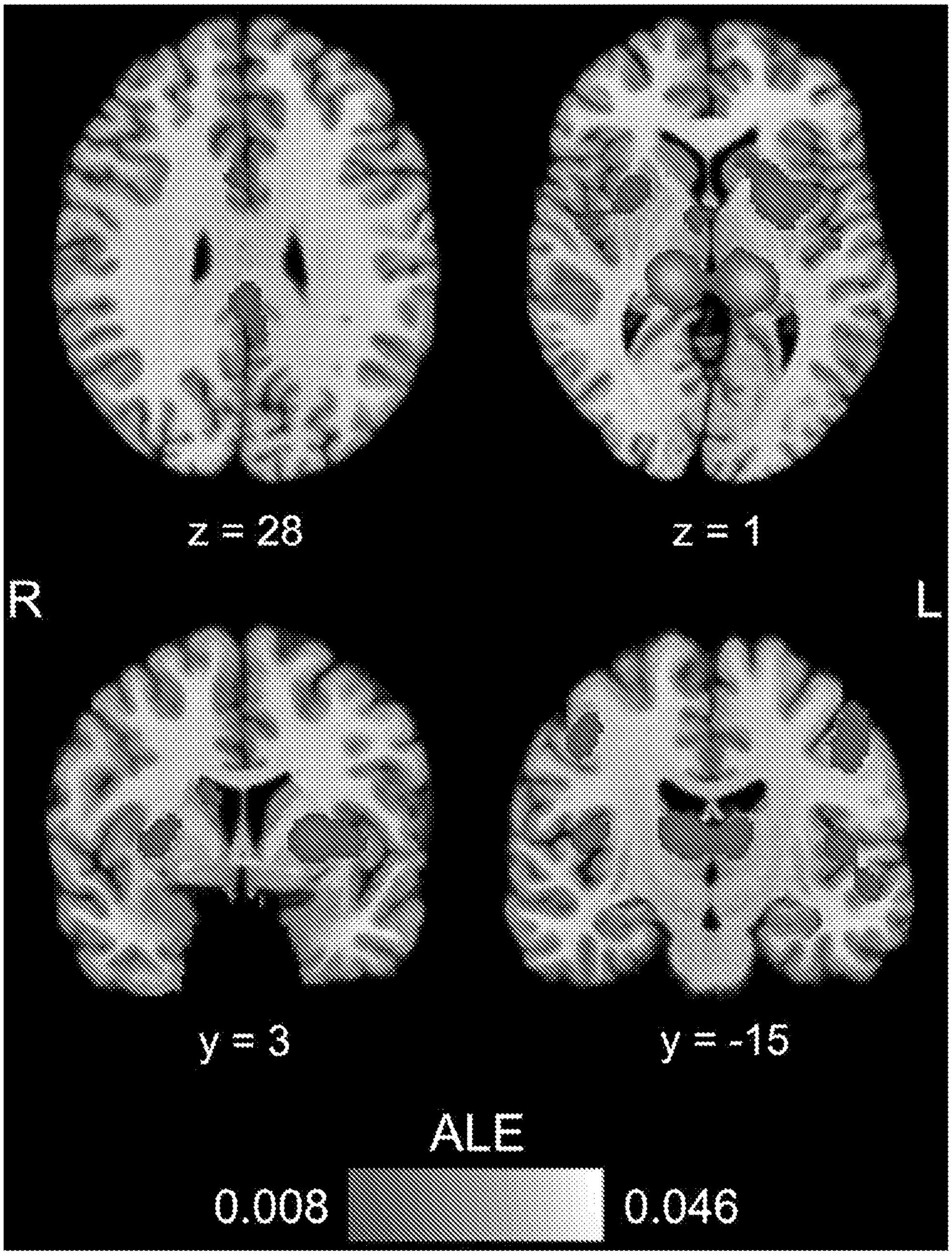
FIGS. 6A-6D are anatomical likelihood estimation (ALE) atrophy maps. A convergent pattern of gray matter atrophy was identified in multiple sclerosis. Regionally selective neurodegeneration affected both cortical and subcortical structures: bilateral thalamic pulvinar, right thalamic medial dorsal nucleus, right caudate body, left caudate head, right anterior cingulate cortex, left posterior cingulate cortex, left claustrum, bilateral insula, bilateral putamen, bilateral precentral gyrus, bilateral postcentral gyrus, and left superior temporal gyrus. ALE results were family-wise error corrected with a cluster-forming threshold of $p<0.001$ and cluster-level inference of 0.05. Results were overlaid on the Colin27 brain template in Montreal Neurological Institute coordinate space.
Figures 7A, 7B, 7C, 7D:
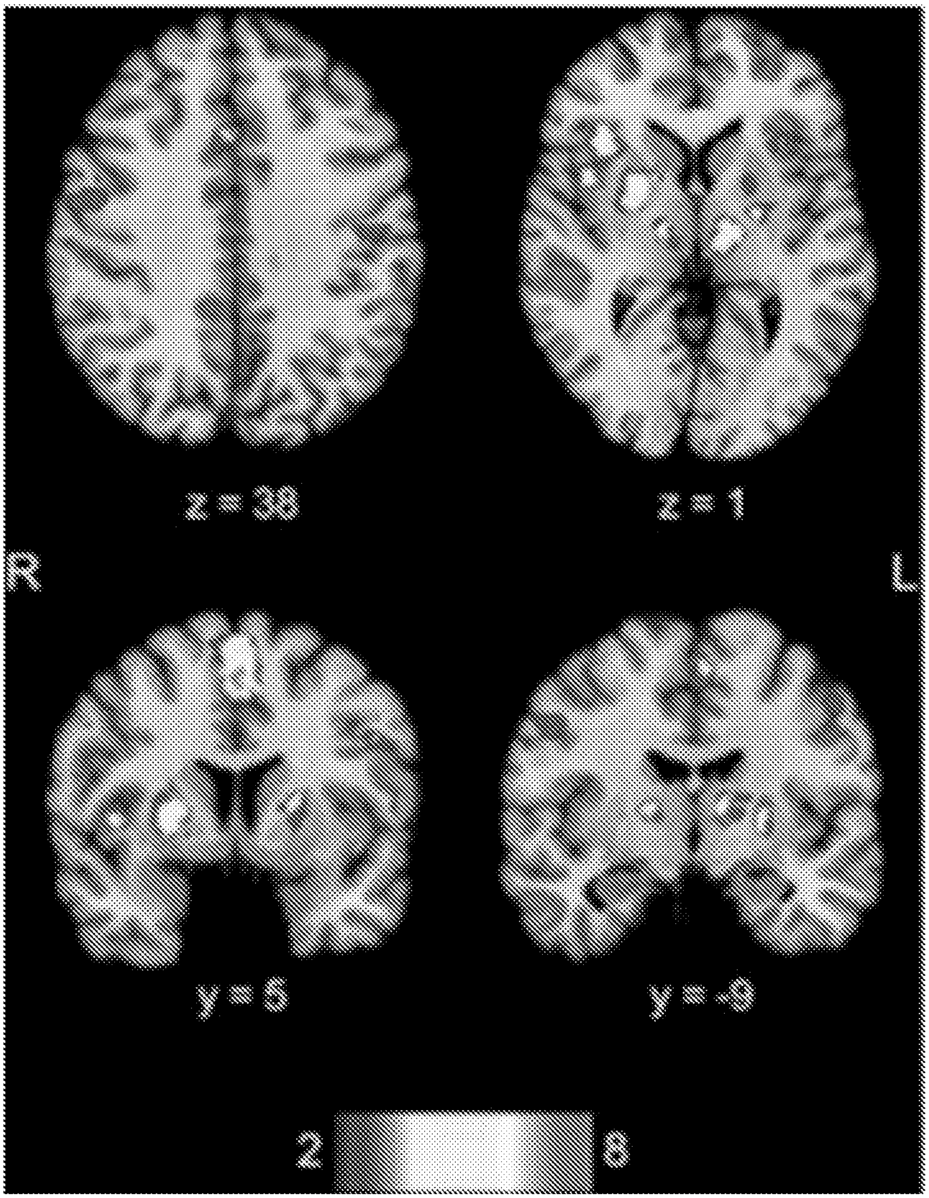
FIGS. 7A-7H are seed-to-whole-brain (SWB) atrophy-based functional network (AFN) model maps.
Figures 7E, 7F, 7G, 7H:
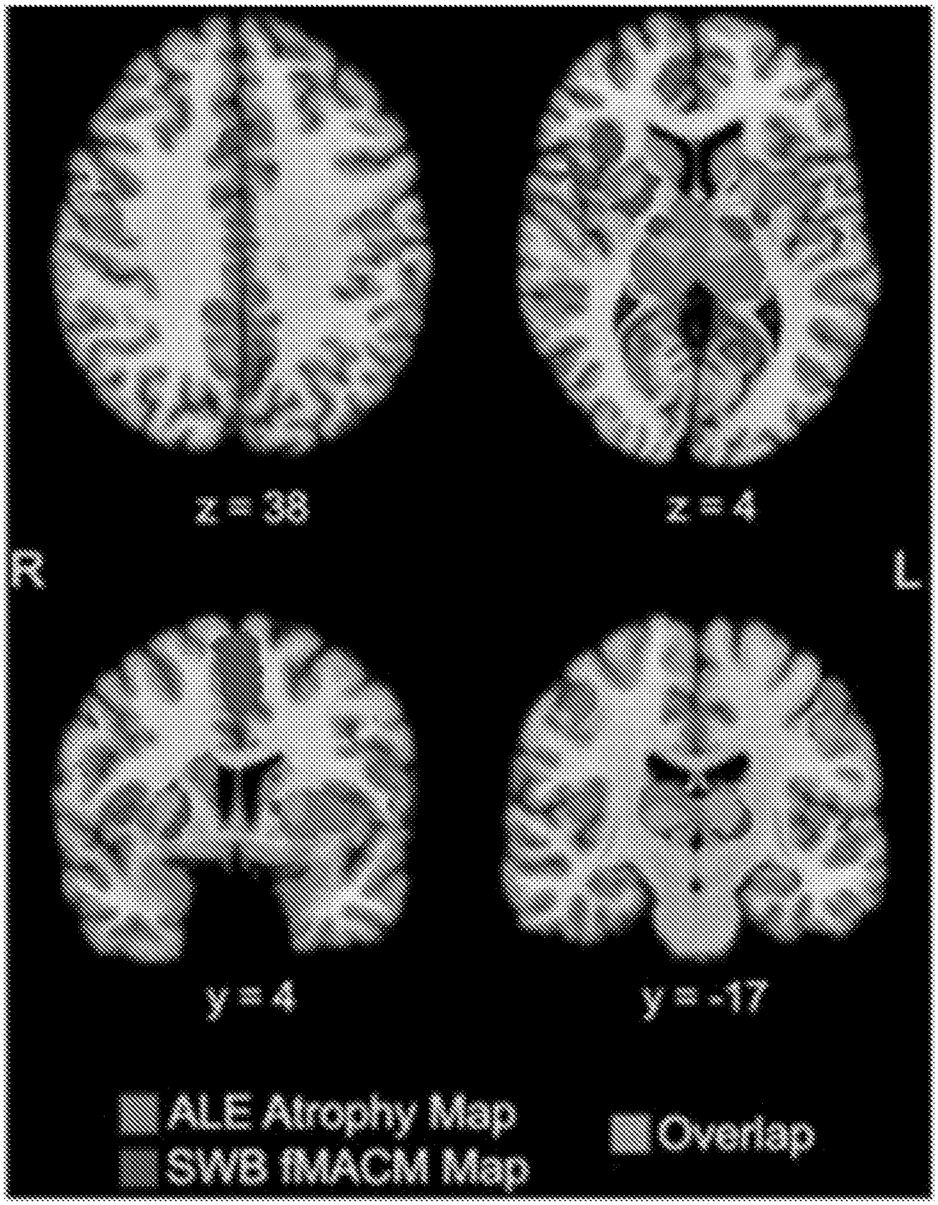

VBM publications considered for meta-analysis were identified in BrainMap using Sleuth (Version 2.4, http://www.brainmap.org/sleuth/). The search logic included: (Diagnosis matches "Any"-either MS or clinically isolated syndrome [CIS]) AND (Contrast is GM). To identify publications not yet in BrainMap, a comprehensive search was performed in PubMed, Science Direct, Web of Knowledge, and Scopus from inception to 19 Oct. 2017 for peer-reviewed English-language journal articles. Keywords for the search included: [("multiple sclerosis" OR "MS"), ("clinically isolated syndrome" OR "CIS")] AND [("voxel-based morphometry" OR "VBM" OR "voxelwise")]. Referenced publications were also searched for additional sources of data. Papers that included x-y-z coordinate-based data in Montreal Neurological Institute (MNI) or Talairach space were coded and submitted to BrainMap using Scribe (Version 3.0, http://www.brainmap.org/scribe/). Submitted papers were published in the database after thorough review and quality control by dedicated support staff. VBM publications identified in BrainMap were reviewed systematically. FIG. 6 is a schematic representation of the systematic review and study selection in coordinate-based meta-analysis. Published voxel-based morphometry studies in MS and clinically isolated syndrome were systematically reviewed for inclusion in the meta-analysis. Study selection adhered to standard quality criteria of BrainMap coordinate-based meta-analysis in addition to the Preferred Reporting Items for Systematic Reviews and Meta-analyses statement. The data were screened for duplication at the paper and experiment level. An experiment is defined as a group contrast resulting in a statistical parametric map. Particular attention was paid to publications by the same authors to avoid redundancy of datasets. Eligibility criteria were applied for study inclusion: whole-brain VBM analysis, results demonstrating GM atrophy, and group contrast of MS or CIS with healthy controls.

Coordinate-based data were exported from BrainMap in MNI standard space using Sleuth (Version 2.4, http://www.brainmap.org/sleuth/) for ALE analysis. Coordinates originally in Talairach standard space were transformed with icbm2tal, which minimizes spatial disparity between Talairach and MNI coordinates, thus facilitating accuracy of CBMA. 29

Data Synthesis and Analysis

Anatomical likelihood estimation (ALE) analysis was performed to determine a consistent pattern of GM atrophy in MS (GingerALE 2.3.6, http://www.brainmap.org/ale/). The defined regions of atrophy (i.e. atrophy seeds/nodes) then served as regions-of-interest (ROIs) in the subsequent AFN analysis. The ALE algorithm treats each coordinate as a Gaussian probability distribution to account for spatial uncertainty. A whole-brain statistical parametric map was created by calculating the spatial convergence (i.e. above-chance clustering) of co-ordinates within and across experiments. Each voxel was assigned an ALE value to reflect the union of these probabilities after mass univariate testing. The statistical significance threshold was determined with a Monte Carlo-based approach to permutation testing. To minimize within-experiment and within-group effects, the optimized ALE algorithm was used, which allows the ALE values to more accurately reflect the degree of foci convergence across studies. The ALE maxima of the cluster results were modelled as three-dimensional (3D) Gaussian point-spread functions to account for error in spatial localization, and the full-width half-maximum of the Gaussians were calculated with the random-effects approach, which scales spatial uncertainty with sample size. 30 Thus, ALE results would be weighted more reasonably toward experiments with larger sample sizes. To avoid overcorrection resulting in an inappropriately small full-width half-maximum, 4 mm was applied to the ALE settings for the VBM dataset.

Each publication utilized voxel-wise group-level comparisons, the methods of which are well-described. The most common source of bias within individual studies was small sample size, which is corrected for in the ALE algorithm. Failure to report negative findings (file-drawer effect) is a form of publication bias that is problematic for meta-analytic computations of effect size but inconsequential for CBMA, which compute cross-study convergence. False-positive effects, on the other hand, are a serious problem for functional neuroimaging, for which CBMA offers a robust solution.

AFN was utilized to assess for functional connectivity involving regions of GM atrophy in a multivariate manner. Seed-to-whole-brain and region-to-region analyses were performed for ROIs defined at atrophy seeds/nodes, which were centered at local ALE maxima from the VBM ALE analysis. For seed-to-whole brain AFN, whole-brain co-activation was tested for each atrophy seed; the co-activation images were then binarized and added spatially using the Multi-image Analysis GUI software (Mango; http://ric.uthscsa.edu/mango/). Additionally, region-to-region AFN was performed for each atrophy seed to identify the most significant functional co-activations. An ROI diameter of 10 mm was used for all AFN analyses, which follows updated guidelines for performing a valid ALE analysis with cluster-level thresholding. The AFN model was constructed using task-evoked fMRI and positron-emission tomography (PET) activations data from healthy controls within BrainMap (2,395 publications, 9,007 experiments, 76,252 coordinates, 39,268 patients, 8,724 conditions).

Thirty-three publications with 45 experiments were included in the VBM ALE analysis, which included 562 co-ordinates and 2,935 patients (1,666 MS patients and 1,269 healthy controls). The dataset fulfils the ALE-specific criteria for determining sufficient power to detect moderate effects, which requires at least 20 experiments within each dataset. Initially, 15 publications were identified in BrainMap; however, after an exhaustive search of online databases, an additional 37 publications were coded into BrainMap. A search of referenced publications did not yield additional sources of data. Twelve experiments were removed with screening procedures for duplication. Application of eligibility criteria excluded 80 experiments in total. All included studies were prospective, and MRI acquisition was evenly distributed on 1.5 and 3 T MRI machines. There were on average 33 patients per group (range=6 to 249) with a female predominance and an average age range of 23 to 54 years. The included papers were published between the years of 2006 and 2017 (mean=2011).

A localised GM atrophy pattern was found to involve both subcortical and cortical structures in MS (Table 1). FIGS. 7A-7D are anatomical likelihood estimation (ALE) atrophy maps. A convergent pattern of GM atrophy was identified in MS. Regionally selective neurodegeneration affected both cortical and subcortical structures: bilateral thalamic pulvinar, right thalamic medial dorsal nucleus, right caudate body, left caudate head, right anterior cingulate cortex, left posterior cingulate cortex, left claustrum, bilateral insula, bilateral putamen, bilateral precentral gyrus, bilateral postcentral gyrus, and left superior temporal gyrus. ALE results were family-wise error corrected with a cluster-forming threshold of $p<0.001$ and cluster-level inference of 0.05. Results were overlaid on the Colin27 brain template in Montreal Neurological Institute coordinate space. These regional effects were demonstrated by seven ALE clusters, with each containing at least one ALE maximum. ALE maxima (in x-y-z coordinates) were found in the bilateral thalamic pulvinar, right thalamic medial dorsal nucleus, right caudate body, left caudate head, right anterior cingulate cortex, left posterior cingulate cortex, left claustrum, bilateral insula, bilateral putamen, bilateral precentral gyrus, bilateral postcentral gyrus, and left superior temporal gyrus. These ALE maxima demonstrated peak convergence of coordinate-based data and were utilized to define the atrophy seeds. Additionally, a cluster was found in the right middle frontal gyrus, which fell just short of the significance threshold. Results were family-wise error corrected for multiple comparisons with a cluster-level inference of 0.05 (cluster-forming threshold, $p<0.001$; number of permutations=1, 000), which are the recommended ALE settings.

TABLE 1

Anatomical likelihood estimation (ALE) clusters.

| Cluster No. | Volume ($mm^3$) | Seed/Node No. | Anatomical Regions | Maximum ALE Value ($\times10^{-3}$) | MINI Coordinates of Local Maxima x | y | z |
|---|---|---|---|---|---|---|---|
| 1 | 29,824 | 1 | Right thalamus, pulvinar | 45.8 | 14 | −26 | 6 |
| | | 2 | Left thalamus, pulvinar | 38.0 | −14 | −28 | 4 |

TABLE 1-continued

Anatomical likelihood estimation (ALE) clusters.

| Cluster No. | Volume ($mm^3$) | Seed/Node No. | Anatomical Regions | Maximum ALE Value ($\times 10^{-3}$) | MINI Coordinates of Local Maxima x | y | z |
|---|---|---|---|---|---|---|---|
| | | 3 | Right thalamus, mediodorsal nucleus | 15.9 | 2 | −8 | 10 |
| | | 4 | Right caudate, body | 12.9 | 14 | 10 | 18 |
| | | 5 | Right anterior cingulate cortex, BA 24 | 9.5 | 4 | 8 | 28 |
| 2 | 7,768 | 6 | Left lentiform nucleus, putamen | 18.0 | −24 | 4 | 2 |
| | | 7 | Left claustrum | 14.0 | −34 | 4 | 2 |
| | | 8 | Left caudate, head | 11.6 | −12 | 18 | −4 |
| 3 | 4,960 | 9 | Right insula, BA 13 | 13.5 | 42 | −16 | 10 |
| | | 10 | Right lentiform nucleus, putamen | 12.1 | 30 | 6 | 0 |
| 4 | 4,792 | 11 | Right precentral gyrus, BA 4 | 13.9 | 46 | −12 | 40 |
| | | 12 | Right postcentral gyrus, BA 3 | 13.4 | 42 | −22 | 50 |
| 5 | 4,208 | 13 | Left precentral gyrus, BA 4 | 12.1 | −46 | −14 | 38 |
| | | 14 | Left postcentral gyrus, BA 2 | 11.4 | −54 | −26 | 44 |
| 6 | 2,112 | 15 | Left insula, BA 13 | 12.5 | −44 | −14 | 6 |
| | | 16 | Left superior temporal gyrus, BA 22 | 10.8 | −54 | −14 | −8 |
| 7 | 2,040 | 17 | Left posterior cingulate cortex, BA 23 | 12.8 | 0 | −34 | 26 |
| 8 | 1,128 | — | Right middle frontal gyrus, BA 9 | 12.5 | 48 | 18 | 30 |

Significant cortico-cortical and subcortico-cortical co-activation patterns involving atrophy seeds were identified. Seed-to-whole-brain AFN results demonstrated co-activations in regions that were consistently atrophied (cluster-forming threshold=0.05, $p<0.001$; number of permutations=1,000); at least two co-activations involve each region of GM atrophy. FIGS. 8A-8H are seed-to-whole-brain (SWB) atrophy-based functional network (AFN) model (AFN) maps. FIGS. 8A-8D demonstrate composite SWB co-activation. The SWB AFN map was created by binarizing and spatially adding SWB results of all atrophy seeds. The number of connections to each seed region ranged from 2 to 8. Conversely, GM regions without atrophy did not demonstrate significant co-activation with the atrophy seeds. FIGS. 8E-8H demonstrate restriction of SWB co-activation. Whole-brain co-activations were localised to regions of GM atrophy in MS. Results were overlaid on the Colin27 brain template in Montreal Neurological Institute coordinate space. Region-to-region AFN testing quantified the co-activations as a connectivity matrix ($e^{2.07}<z<8.21$). FIG. 9A is a AFN connectivity matrix. Inter-regional co-activations were present in GM affected by atrophy in MS. The most significant co-activations are highlighted ($z>5.00$).

The inter-regional co-activation results were Bonferroni-corrected ($p<0.001$, $z>2.97$) for 34 co-activations (Table 2). The most significant co-activations ($z>5.00$) were identified as follows: left precentral gyrus and right precentral gyrus, right putamen and left putamen, left precentral gyrus and left putamen, left claustrum and left putamen, as well as right putamen and left claustrum. Significant co-activations with $4.00<z<5.00$ were demonstrated between homotopic anatomical structures in the insula and thalamic pulvinar. Additionally, several co-activations were noted with $3.00<z<4.00$: right medial dorsal nucleus and left putamen, left precentral gyrus and right putamen, right precentral gyrus and left putamen, left postcentral gyrus and left pulvinar, right medial dorsal nucleus and right pulvinar, as well as left postcentral gyrus and right postcentral gyrus. Co-activation remained significant but relatively weaker between the right postcentral gyrus and right precentral gyrus. Region-to-region AFN results were visualized as a node-and-edge model in Brain Net Viewer. FIG. 9B is an AFN node-and-edge model. Functional connectivity between regions of atrophy were demonstrated ($p<0.001$, $z>2.97$, corrected for multiple comparisons). The most significant results indicate involvement of the corticostriatal network ($z>5.00$). These paths can be tested as predictors of disease-related changes in resting-state fMRI. Network seed and node abbreviations: right, R; left; L; precentral gyrus, Pre; postcentral gyrus, Post; insula, Ins; claustrum, Claus; thalamic pulvinar, Pulv; thalamic medial dorsal nucleus, MDN; putamen, Put; superior temporal gyrus, STG; head of caudate, CaudH; body of caudate, CaudB; posterior cingulate cortex, PCing; anterior cingulate cortex, ACing.

TABLE 2

Region-to-region AFN co-activations.

| Seed | Meta-analytic co-activation (z) | Node |
|---|---|---|
| L Pre | 8.43 | R Pre |
| R Put | 7.13 | L Put |
| L Pre | 6.57 | L Put |
| L Claus | 6.01 | L Put |
| R Put | 5.17 | L Put |
| R Ins | 4.44 | L Ins |
| R Pulv | 4.19 | L Pulv |
| R MDN | 3.80 | L Put |
| L Pre | 3.67 | R Put |

TABLE 2-continued

Region-to-region AFN co-activations.

| Seed | Meta-analytic co-activation (z) | Node |
|---|---|---|
| R Pre | 3.59 | L Put |
| L Post | 3.22 | L Pulv |
| R MDN | 3.20 | R Pulv |
| L Post | 3.18 | R Post |
| R Post | 2.97 | R Pre |

Significant co-activations involved localised regions of grey matter atrophy in multiple sclerosis ($p < 0.001$, $z > 2.97$, corrected for multiple comparisons).
Network seed and node abbreviations: right, R; left; L; precentral gyrus, Pre; postcentral gyrus, Post; insula, Ins; claustrum, Claus; thalamic pulvinar, Pulv: thalamic medial dorsal nucleus, MDN; putamen, Put.

In this two-stage meta-analysis in MS, both hypotheses were confirmed. First, this study demonstrated that GM atrophy was regionally selective; and second, that these brain regions were connected functionally. The present findings suggest that neurodegeneration in MS does not occur randomly. Moreover, the functional organization of these regions may provide an explanation for localized GM atrophy in MS. By using CBMA, a data-driven functional network model was created. This laboratory non-specific analytic prior is intended to guide future targeted quantitative analysis of primary datasets in MS.

A pattern of localized GM atrophy was identified cortically and subcortically, predominantly involving the thalamus, basal ganglia, sensorimotor cortex, and cingulate gyrus. This ALE pattern of atrophy is highly similar to that reported in other recent studies; that is, the effects converge with prior studies describing regional selectivity of GM atrophy. Although the pathophysiology of localized GM atrophy in MS is unclear, several causes have been suggested, including: cerebrospinal fluid (CSF)-mediated inflammation of GM; axonal transection leading to trans-synaptic degeneration; cytotoxic tissue damage secondary to lymphoid tissue formation; neuronal mitochondrial dysfunction; and antigenic variability in neuronal sub-populations. Although these theories are plausible, they do not fully account for the specific pattern of localized GM atrophy. Therefore, the NDH was tested, which addressed regional GM atrophy at the whole-brain level.

Using disease-specific nodes (from the ALE analysis), functionally covariant GM regions were observed in healthy controls using AFN. These regions are members of a functional network that is selectively attacked by MS. Although the AFN model does not indicate functional abnormality in MS, the results do describe the healthy functional organization of these nodes. This model-based hypothesis was tested with the expectation that the model fit would be degraded in MS. To validate the AFN model, a seed-to-whole-brain analysis was performed, followed by a region-to-region analysis. The seed-to-whole-brain approach ensured that the AFN results were not biased by restriction to pre-defined nodes. The region-to-region analysis quantified connectivity strength per path. The present findings indicate a pattern of co-activation involving GM regions that were consistently affected by atrophy. Further, GM not affected by atrophy did not display significant co-activation with the atrophy seeds; that is, co-activations were restricted to regions of atrophy. Thus, the AFN model supports that localized GM atrophy in MS is network-based.

The NDH emerged from observations in neurodegenerative disorders causing cognitive and motor performance degradation. Distinct, non-random, disease-specific atrophy patterns were observed in Alzheimer's disease, fronto-temporal dementia, and Parkinson's disease; in each instance, the affected brain regions appeared to be functionally connected, i.e., form functional networks. These observations have been interpreted to mean that GM atrophy in degenerative disorders is network-based. In MS, the concept of "hubs" (i.e. nodes that are more connected to other nodes) has been suggested as an explanation of the non-random atrophy pattern, a possible extension of the NDH. The implication is that GM atrophy initially affects hub regions and subsequently involves functionally connected non-hub brain regions; however, validation of this temporal sequence would necessitate longitudinal evaluations. Additionally, it has been suggested that WM pathology may drive the initial atrophy at the local level in hub regions, which then has "second-order effects" resulting in atrophy of functionally connected brain areas. The present results are in line with this concept, wherein the second-order effects are facilitated by network connectivity be-tween regions of localised GM atrophy; however, the initial involvement of WM pathology is unlikely to fully capture the pathophysiology of MS given the limited correlation of WM lesions with clinical progression. All in all, the NDH is a reasonable consideration for explaining the pathophysiology of non-random GM atrophy in MS.

Impaired signal transmission in cortico-subcortical functional networks in MS has been linked to physical disability and cognitive dysfunction. Specifically, it has been reported that the cortico-striatal network may be affected, which is compatible with the motor, cognitive, and affective symptom profile in MS. The present AFN results demonstrate the highly significant functional connectivity of the putamen with the primary motor cortex and thalamus. Neuro-anatomically, the cortico-striatal-thalamo-cortical circuitry involves projections from multiple cortical regions to the basal ganglia. The striatum-composed of the caudate, putamen, and nucleus accumbens-serves as the primary input structure. Efferent signals are then relayed to specific cortical regions. A commonly accepted functional model of the basal ganglia involves topographically organized and functionally segregated circuitry, with the final segment terminating in motor, cognitive, and limbic cortical regions. Additionally, functional parcellation of the striatum has demonstrated distinct functional connectivity profiles for each striatal sub-region. Further, CBMA and neurophysiological studies have characterized the striatal functional distribution as exhibiting a ventro-dorsal gradient with cognitive motor topology; however, it has been suggested that there is complex integration of information across functional subdivisions of the basal ganglia prior to information output back to the frontal cortex. Therefore, although the AFN results suggest that the motor component of the corticostriatal network is involved in MS, cognitive and limbic processes may also play a role in refining motor function prior to the execution of goal-directed behaviors.

The motor component of the corticostriatal network has been reported to receive projections from several cortical areas including the primary motor, supplementary motor, premotor, and somatosensory cortices. In resting-state fMRI of MS, increased functional connectivity of the pre-motor area and dorsal caudal putamen appears to be associated with motor decline as demonstrated by positive correlation with the Expanded Disability Status Scale. Additionally, there is evidence to suggest that the cortico-striatal network is affected in postural adaptation as well as acquisition and retention of motor skills in MS. These prior findings are supported neuro-anatomically in that brain regions receiving subcortical output includes the supplementary motor area, which is important in programming and control of movement. Taken together with these observations, the present results suggest that motor integration may be affected in MS due to involvement of the corticostriatal network.

Although conventional MRI methods provide valuable clinical information in vivo, more advanced techniques are necessary to improve standard-of-care imaging in MS and solidify our understanding of the neurodegenerative pathophysiology. Currently, clinical imaging relies on lesion detection using T1- and T2-weighted techniques; however, due to the recent reports of GM atrophy in MS, it is evident that there is a need for more sensitive imaging methods to characterize neurodegenerative changes. Given that GM atrophy is not readily apparent on visual assessment, quantitative neuroimaging analysis offers improved evaluation of GM pathology. For analysis of T1-weighted MRI, VBM can identify subtle focal GM atrophy, but this technique is limited in that group-level comparisons are achievable. On the other hand, analysis of fMRI has the potential to enrich the imaging-based armamentarium in the clinical setting via individualized evaluation. To this end, functional connectivity measures can be examined using fMRI time series data to provide per-subject level information. Additionally, it has been shown that fMRI is a more sensitive method in detecting abnormalities when compared with structural imaging, which may help diagnose MS earlier in the course of disease or pre-clinically. Nevertheless, to avoid laboratory-specific bias, the development of a functional imaging tool would benefit from a meta-analytic model-based approach prior to analysis of primary functional imaging data.

In this study, ALE and AFN were used sequentially to characterize consistent findings from existing primary studies, the results of which can be applied stepwise in primary fMRI data. This modelled approach provides a selection of quantitative imaging measures that could be incorporated into diagnostic algorithms to enhance clinical evaluation of MS patients. Specifically, the most significant functional co-activations from AFN can be tested as predictors of disease-related change in resting-state fMRI. AFN has been validated in resting-state fMRI data and can be applied directly in imaging results of MS patients and healthy controls. Using this technique, a functional connectivity model with improved generalizability was constructed, which capitalizes on an extensive compilation of published neuroimaging literature and addresses the limited sample sizes of individual primary studies. In contrast to task-based fMRI, utilization of resting-state fMRI is well-suited for the clinical setting and has the benefit of evaluating network-based changes without the complexity of task-performance testing or the confounding effects of task-performance variation. Further, it has been shown that brain activity during activation and rest are correspondent, as demonstrated by a study comparing results of independent component analysis using BrainMap task-based fMRI data and primary resting-state fMRI data. Therefore, the co-activation pattern determined by AFN can guide subsequent analysis of resting-state fMRI data to characterize functional connectivity changes in MS.

Structural and functional covariance patterns may be closely related. The correspondence between structure and function has been described by network-based trophic influences that may shape structural modification of the brain. More recently, a longitudinal study in MS reported that structurally and functionally related brain regions may demonstrate accelerated tissue loss in patients who progress in clinical disability. Furthermore, it has been shown that structural covariance of localized regions of the brain could be detected prior to overt atrophy. Given the limitations in identifying GM atrophy patterns at a per-subject level, particularly in early disease, structural covariance may serve as an alternative imaging-based measure of regionally selective neurodegeneration in MS. Other considerations may be to refine the meta-analytic models by applying connectivity-based parcellation and behavioral filtering to BrainMap data; this would improve targeted functional connectivity testing in primary data via identification of pertinent clinical features.

GM atrophy exists in MS affected localized brain regions that were functionally connected. Consistent, regionally selective neurodegenerative changes were identified. Inter-regional co-activations were characterized meta-analytically. The functional network model serves as a framework for future quantitative analysis of per-subject resting-state fMRI data. Such individualized imaging metrics should inform future diagnostic and prognostic imaging marker development strategies.

Example 3

The AFN model is used to predict biomarkers in rsfMRI. To this end, network-based biomarker development was undertaken while drawing from the robust existing neuroimaging literature.

Materials and Methods

Whole-brain rsfMRI was acquired for 20 MS (M/F=8/12; age=36.30±8.94; EDSS 4.0 (1.0-8.0); disease duration 7.85±5.45) and 20 age- and sex-matched HC. After image preprocessing, timeseries extraction was performed at ROIs specified by the AFN model. For AFN paths, standardized semi-partial regression coefficients based on maximum likelihood estimation were computed via structural equation modeling then Fisher's z transformed. Between-group alteration was determined per path with the Mann-Whitney U test. The paths found to be significantly different were included as predictors in logistic regression models; based on the probability estimates, ROC curves were derived to demonstrate overall diagnostic accuracy. All statistical analyses were performed in SPSS, Version 25 (Chicago, Ill).

Five of the paths in the AFN model demonstrated significantly decreased functional connectivity in MS when compared with HC ($p<0.05$). FIG. 10 is a representation of the atrophy-based functional network (AFN) model (AFN). The AFN node-and-edge model was applied in a prospective resting-state fMRI dataset. Five paths predicted by the AFN model demonstrated significantly decreased functional connectivity in MS when compared with healthy controls, $p<0.05$ (pink). Network seed and node abbreviations: right, R; left; L; precentral gyrus, Pre; postcentral gyrus, Post; insula, Ins; claustrum, Claus; thalamic pulvinar, Pulv; thalamic medial dorsal nucleus, MDN; putamen, Put; superior temporal gyrus, STG; head of caudate, CaudH; body of caudate, CaudB; posterior cingulate cortex, PCing; anterior cingulate cortex, Acing; middle frontal gyrus, MFG.

The five-path network predictor resulted in an area under the curve (AUC) of 0.80 (FIG. 11). The AFN model yielded a promising network-based imaging marker in rsfMRI. FIG. 11 is a graphical representation of the diagnostic accuracy of the AFN. The receiver operating characteristic curve (ROC) curve of the five-path predictor resulted in an area under the curve (AUC) of 0.80 [asymptotic 95% CI=0.66, 0.93]. This study showcased a stepwise approach in applying a meta-analytically constructed network model to a distinct, prospective dataset. Furthermore, model-based hypothesis testing was carried out without the constraints of intralaboratory idiosyncrasies in building the applied network model. Therefore, the results suggest that these network-based functional imaging metrics could improve diagnosis of MS in the clinical setting.

Example 4

By using the AFN method, a localized pattern of grey matter atrophy was confirmed in MS and the presence of functional connectivity was observed between these brain regions in healthy subjects. The AFN results can serve as a model-based null hypothesis, which could then be tested via region-to-region functional connectivity analysis in prospectively acquired resting-state fMRI. The expectation is that, in MS, these functional connections would deviate from the network structure specified by the model. In this Example, a functional network imaging tool in MS was developed by applying the AFN model in resting-state fMRI (FIG. 12). FIG. 12 is a AFN functional network model. A meta-analytical network model with nodes and edges representing localized regions of grey matter atrophy and inter-regional functional connectivity, respectively. This targeted biomarker discovery strategy involves assessment of the functional network predicted by AFN in a distinct, prospectively acquired dataset. There would be increased deviation in model fit with worsening of clinical disability. To this end, network-based biomarker development was undertaken while drawing from current neuroimaging literature.

Twenty study participants with relapsing-remitting MS and 20 age- and sex-matched healthy volunteers were prospectively recruited between September 2018 and January 2019. Inclusion criteria of MS subjects were age 18-50 years and fulfillment of 2010 revised McDonald criteria for relapsing-remitting MS. Exclusion criteria were clinical relapse or use of steroid medications within the past month, structural brain disease, prior brain surgery, uncontrolled psychiatric condition, and claustrophobia or other contraindications to MR imaging. All enrolled participants met all inclusion criteria. Five recruited subjects were withdrawn due to the following reasons: screen failures (2), excessive imaging artifact (2), and incidental brain structural abnormality (1). Characteristics of MS and healthy control subjects are summarized in Table 3.

TABLE 3

Characteristics and Clinical Status of Relapsing-Remitting Multiple Sclerosis Patients and Healthy Control Subjects.

| Characteristics and Clinical Status | Relapsing-Remitting Multiple Sclerosis Patients | Healthy Control Subjects |
|---|---|---|
| N | 20 | 20 |
| Age (year) | 36.30 ± 8.94 | 36.20 ± 9.75 |
| Sex (M/F) | 8/12 | 8/12 |
| EDSS | 4.0 (1.0 - 8.0) | NA |
| Disease Duration (year) | 7.85 ± 5.45 | NA |
| NLV (mL) | 10.11 ± 12.36 | NA |
| NGMV (L) | 0.82 ± 0.14 | 0.84 ± 0.11 |
| NWMV (L) | 0.76 ± 0.11 | 0.73 ± 0.08 |
| NCSFV (L) | 0.47 ± 0.07 | 0.45 ± 0.08 |
| NWBV (L) | 1.58 ± 0.22 | 1.57 ± 0.19 |

EDSS, Expanded Disability Status Scale; NA, Not Applicable; NLV, normalized lesion volume; GMV, grey matter volume; WMV, white matter volume; CSFV, cerebrospinal fluid volume; WBV, whole brain volume.
Data are mean = standard deviation.
Data in parentheses are the range.

Whole-brain MR imaging was acquired with a 3 T Siemens TIM-Trio (Siemens Medical Solutions, Erlangen, Germany) using a standard 12-channel head coil as the RF receiver and the integrated circularly polarized body coil as the RF transmitter. Functional T2*-weighted MRI (BOLD) was acquired using a multi-band gradient-echo echo-planar imaging sequence with agreement from University of Minnesota (Xu et al. 2013). A total of 700 volumes were acquired with the following parameters: TR/TE=1400/30 ms; flip angle=52°; FOV=211×211 mm; base resolution=88×88; multi-band acceleration factor=3; and 2.4 mm isotropic voxel size. Subjects were given instructions to remain awake with their eyes closed and to let their minds wander. Dummy scans were performed to establish steady-state magnetizations. To correct for distortions, a gradient-echo fieldmap was acquired with the same shimming and acquisition matrix. 3D T1-weighted images were obtained using the MPRAGE pulse sequence with TR/TE/TI=1900/2.26/900 ms, flip angle=9°, FOV=256×256, in-plane image matrix=256, and 1 mm isotropic voxel size. T2-weighted FLAIR imaging was obtained using the 3D turbo spine echo sequence to characterize lesion volume; acquisition parameters included TR/TE/TI=5000/335/1800 ms; echo train duration=673 ms, echo spacing=3.1 ms, turbo factor=221, 160 sagittal sections; FOV=256×256; in-plane image matrix=256×256; and 1 mm isotropic voxels.

All acquired images were visually inspected for quality control prior to image analysis. Functional data preprocessing was performed using FSL (FMRIB Software Library, version 5.0.11, www.fmrib.ox.ac.uk/fsl). The FEAT software package was used for data preprocessing which included linear registration to T1-weighted images and nonlinear registration to the MNI152 template, motion correction, fieldmap unwarping, slice timing correction, brain extraction, spatial smoothing with 5 mm FWHM, and temporal filtering with a high-pass filter of 100 s. Additional noise-reduction steps included removal of motion-related artifacts using an automated ICA-based strategy (Pruim et al. 2015). Further, nuisance regression was performed by using the mean signal of white matter and cerebrospinal fluid as regressors (Pruim et al. 2015).

The workflow in applying the AFN model in rsfMRI is shown in FIGS. 13A and 13B. FIG. 13A shows AFN as applied in rsfMRI data to sample the timeseries. FIG. 13B is a graphical representation of the rsfMRI timeseries that serves as an observed variable in the structural equation modeling path analysis. ROIs (radius=5 mm) defined by the AFN model were used to extract the mean timeseries across the 4D-rsfMRI data. Binary ROIs drawn at AFN-specified nodes were transformed from standard (MNI) to the native EPI space of each subject with nonlinear registration. The ROIs were re-binarized to minimize effects of interpolation. Next, each ROI was used to sample the 4D volumetric rsfMRI data and extract the mean timeseries values.

White matter lesions were segmented by the lesion growth algorithm as implemented in the LST toolbox version 2.0.15 (www.statistical-modelling.de/lst.html) for SPM (version 12). The algorithm first segments the T1 images into the three main tissue classes (cerebrospinal fluid, grey matter, and white matter). This information is then combined with the coregistered FLAIR intensities in order to calculate lesion belief maps. By thresholding these maps with a pre-chosen initial threshold (κ=0.3) an initial binary lesion map is obtained which is subsequently grown along voxels that appear hyperintense in the FLAIR image. The optimal initial threshold was determined by two board-certified neuroradiologists by visual inspection. The resulting lesion probability map was thresholded to obtain a binary lesion segmentation. The total lesion volume was normalized for head size, resulting in normalized lesion volume (NLV).

To minimize the effect of T1 hypointensities on brain volumetric measurements, T1-weighted images were preprocessed using the lesion_filling tool in FSL. Subsequently, the SIENAX software was used to obtain global brain tissue volumes, normalized for head size.

Structural equation modeling (SEM) was used to assess the model fit of AFN in each group of subjects and also for MS subjects individually. All SEM analyses were performed in Statistical Package for the Social Sciences Amos, version 25.0 (SPSS, Chicago, Ill) and are based on the computation of standardized semi-partial regression coefficients using maximum likelihood estimation. In the SEM path diagram, observed variables and paths were specified by the nodes and edges in the AFN model, respectively. To better represent temporal effects in fMRI timeseries data, a unified SEM approach with multivariate autoregressive modeling was taken. A standard recursive SEM model was constructed, so the stronger path in bidirectional AFN coactivations was retained in the path diagram. The root mean square error of approximation (RMSEA) was selected as the primary fit criterion given its relative insensitivity to the effects of a small sample size; an RMSEA of <0.08 indicates a reasonably good fit to the data. Prior to model testing, an exploratory Bayesian model selection procedure was followed to optimize the final model. Remaining statistical analyses were performed in SPSS, version 25.0 (Chicago, Ill). Pearson correlation coefficients were computed between per-subject clinical data (EDSS scores and disease duration) and imaging metrics (RMSEA, NLV, and other brain volumetric measurements listed in Table 3).

The final AFN model included 18 region-to-region paths (FIG. 9). FIG. 9 is a schematic representation of the AFN Applied as a Path Diagram in Structural Equation Modeling (SEM). The path diagram demonstrates the functional network structure used to compute the group-level model fit using AFN. the acquired rsfMRI of relapsing-remitting multiple sclerosis patients and healthy control subjects. The specified network demonstrated a good model fit in both MS and healthy control participants (Table 4). The final AFN model was applied in resting-state fMRI of both MS and healthy control subjects. The Root Mean Square Error of Approximation (RMSEA) point estimates and confidence intervals were computed for each group; RMSEA <0.08 indicates a good fit.

TABLE 4

Group-level model fit of the final AFN model.

| Subject Group | RMSEA | 90% Confidence Interval |
|---|---|---|
| Relapsing-Remitting Multiple Sclerosis Patients | 0.069 | 0.069-0.070 |
| Healthy Control Subjects | 0.079 | 0.078-0.079 |

For MS subjects, the AFN model achieved an RMSEA of 0.069 (90% CI=0.069-0.070). For healthy control subjects, the AFN model achieved an RMSEA of 0.079 (90% CI=0.078-0.079). These model fit results showed a groupwise difference (ARMSEA) of 0.01. While regression analyses in SEM are based on classical statistics, significance level testing does not directly apply in interpretations of SEM results. However, a groupwise ARMSEA of 0.01 has been reported to be a statistically and practically important groupwise difference in model fit. This was an important groupwise distinction prior to post hoc analysis.

Univariate associations between subject-level imaging findings and clinical data were computed via Pearson correlations (FIG. 14). FIG. 14 is a correlation of imaging and clinical characteristics in Multiple Sclerosis. Double bar graphs display strength of univariate associations between various imaging and clinical measures. The asterisk denotes statistically significant correlation results in RMSEA with EDSS (p=0.002). EDSS, Expanded Disability Status Scale; RMSEA, Root Mean Square Error of Approximation; NLV, normalized lesion volume; GMV, grey matter volume; WMV, white matter volume; CSFV, cerebrospinal fluid volume; WBV, whole brain volume. Correlations of RMSEA and EDSS resulted in a large effect size which was statistically significant (r=0.647, p=0.002); correlations of RMSEA and disease duration showed a small effect size without meeting the significance threshold (r=0.253, p=0.282). Correlations of CSFV and EDSS showed a medium effect size which was borderline significant (r=0.403, p=0.078); correlations of CSFV and disease duration showed a small effect size without meeting significance threshold (r=−0.251, p=0.286).

Remaining correlation analyses yielded overall small effect sizes without meeting significance threshold. Correlations of NLV with EDSS (r=−0.071, p=0.766) and NLV with disease duration (r=0.001, p=0.998) both showed negligible associations. Correlations of GMV with EDSS (r=0.209, p=0.377) and GMV with disease duration (r=0.017, p=0.944) resulted in small effect sizes. Correlations of WMV with EDSS (r=0.096, p=0.687) and WMV with disease duration (r=−0.115, p=0.628) resulted in negligible to small effect sizes. Correlations of WBV with EDSS (r=0.172, p=0.469) and WBV with disease duration (r=−0.045, p=0.849) also resulted in negligible to small effect sizes.

The largest effect sizes were demonstrated in the correlation results of RMSEA; the correlation between RMSEA and EDSS was a univariate association meeting significance threshold. In contrast, the smallest effect sizes were demonstrated in the correlation results of NLV. These results are displayed as scatterplots (FIGS. 15A-15D). FIGS. 15A-15D are scatterplots of RMSEA and Disease Burden. Per-subject RMSEA was correlated with EDSS and disease duration. The correlation results for NLV are included for comparison. The highest proportion of explained variance is noted in the relationship between RMSEA and EDSS.

Results from this study show that the AFN model predicted functional network abnormalities in MS on resting-state fMRI. Two predictions were confirmed: (1) the meta-analytically derived AFN model can be reasonably applied to prospectively acquired resting-state fMRI; and (2) the degree of functional connectivity deviation from the AFN model has a strong association with clinical disability (i.e. as model fit worsened, clinical disability increased). In contrast, correlations between tested volumetric imaging metrics with clinical measures were relatively weak. For example, correlations of NLV with EDSS and NLV with disease duration resulted in negligible associations. By applying the meta-analytically derived AFN model in prospective resting-state fMRI data, a quantitative functional imaging biomarker was identified in MS.

This study used a unified SEM approach as a statistical strategy for applying the AFN model in resting-state fMRI. Although the AFN model fits relatively well in resting-state fMRI data of both MS and healthy control subjects, there was a statistically and practically important groupwise difference in model fit. However, given that fit indices yield information bearing predominantly on the model's lack of fit and do not reflect the extent to which the model is plausible, assessment of model adequacy must be based on additional criteria that takes into account theoretical, statistical, and practical considerations. Thus, post hoc correlation analysis was subsequently performed using RMSEA and clinical metrics. The results show that there is a strong positive clinical correlation between RMSEA and EDSS. The correlation between RMSEA and disease duration was relatively weaker, which could be related to heterogeneity in medication regimen, compliance, and treatment response. Table 5 is a correlation table of imaging output and clinical characteristics. Relationship between imaging output and clinical metrics of disease burden were computed as semi-partial correlation coefficients (r). The strongest association was found between RMSEA and EDSS, which was statistically significant (p=0.002).

TABLE 5

Correlation Table of Imaging Output and Clinical Characteristics.

| | EDSS (r) | Disease Duration (r) |
|---|---|---|
| RMSEA | 0.647*, p = 0.002 | 0.253, p = 0.282 |
| NLV | −0.071, p = 0.766 | 0.001, p = 0.998 |
| GMV | 0.209, p = 0.377 | 0.017, p = 0.944 |
| WMV | 0.096, p = 0.687 | −0.115, p = 0.628 |
| CSFV | 0.403, p = 0.078 | −0.251, p = 0.286 |
| WBV | 0.172, p = 0.469 | −0.045, p = 0.849 |

EDSS, Expanded Disability Status Scale; RMSEA, Root Mean Square Error of Approximation; NLV, normalized lesion volume; GMV, grey matter volume; WMV, white matter volume; CSFV, cerebrospinal fluid volume; WBV, whole brain volume.

Relationship between imaging output and clinical metrics of disease burden were computed as semi-partial correlation coefficients (r). The strongest association was found between RMSEA and EDSS, which was statistically significant (p=0.002). The results of this study demonstrated that functional network connectomics are an important component in improving understanding of localized grey matter atrophy in MS. It should be pointed out that functional co-activations in AFN were previously computed using task-activation fMRI and PET data. However, the present analysis was conducted in data unrelated to the meta-analytic precursor (i.e. in resting-state fMRI). Specifically, cross-modality validation of the AFN model was provided by results of this study and are of two types. First, the meta-analytic model predicted primary data results. Second, functional task-based data predicted resting-state observations. This network-based imaging biomarker development strategy suggests that an atrophy-based functional network is likely involved in the pathophysiology of regionally specific grey matter atrophy in MS.

The observations made in this study corroborate recent findings of functional network integrity breakdown in MS. Since it may be overly simplistic to evaluate functional connections individually, a network-based approach was opted. In this study, there was increasing disruption of the AFN model fit as disease severity worsened. In inter-regional functional connectivity analysis, one of the most critical steps is defining the ROI. While nodal definition in this study is based on meta-analytically convergent regions of atrophy in MS, studies using other methods to define nodes have also reported similar findings of network disruption (e.g. random cortical parcellation and ICA-based methods). In addition, analysis using regional homogeneity (ReHo) reveals disrupted intra-regional synchronized activity in affected brain regions such as the caudate and insula. The findings in this study are in line with current reports of functional network alterations in MS, although there is still debate on more specific characteristics of functional connectivity changes and whether these changes are part of a passive or active process. However, network reorganization is likely a dynamic process, and there is a need for more research to better describe functional network alterations in MS.

In the clinical setting, the findings from this study would offer a robust model that could be useful for diagnosis or prognosis. Since AFN identifies a "core" functional network that is most consistently affected in MS, additional connections that are variably involved likely coexist. However, to account for clinical variability and enable widespread utility, surveillance of the core functional network is relatively more important in the clinical setting. Interestingly, nodes in the AFN model include previously described network hubs, or regions that are most well-connected, including superior frontal and parietal cortices as well as subcortical putamen and thalamus. Practically, the evaluation of localized grey matter atrophy may be of limited clinical utility since atrophy often indicates the presence of irreversible brain tissue loss. In contrast, evaluation of perfusion to specific brain regions may allow characterization of transient functional changes prior to permanent structural damage. Specifically, fMRI measures cerebral blood flow as a surrogate marker of brain activity. In particular, resting-state (i.e. task-free) fMRI is useful in the clinical setting (as opposed to task-based fMRI) given its non-dependence on task-performance variation. Additionally, functional connectivity analysis using resting-state timeseries data enables individualized assessment. This advantage of functional imaging analysis overcomes the limitations associated with quantitative assessment of structural imaging, which relies on group-level data. Overall, the AFN model helps to identify replicable neuroimaging features which could be used to develop sensitive imaging tools for evaluating individual patients. The AFN model, as a result of data-reduction, is an appropriately complex model in the setting of a small sample. Expansion of the cohort would allow the use of additional parameters without concerns of saturating the model, which could yield additional imaging biomarkers. This study showcased a stepwise approach in imaging biomarker discovery in MS via targeted (meta-analytically optimized) assessment of functional network abnormalities. By examining functional connectivity predicted by the AFN model, network alterations involving consistently atrophic grey matter regions were identified. Present findings encourage further development of the AFN model as a clinical tool to diagnose and closely monitor disease progression in MS.

Numerous benefits have been described which result from employing the methods and systems described herein. The foregoing description of the one or more forms has been presented for purposes of illustration and description. Modifications or variations are possible in light of the above disclosure.

What is claimed is:

1. A method for diagnosing and addressing multiple sclerosis (MS), the method comprising:

acquiring an input including functional MRI (rsfMRI) data, of a brain of a subject;

preprocessing the input via one or more of motion correction, B0 warping, slice timing correction, and spatial smoothing to thereby form a preprocessed input including gradient-echo fieldmap data of the rsfMRI data or T1-weighted data;

applying the preprocessed input to an atrophy-based functional network (AFN) model, the AFN model comprising nodes defined by regions of grey matter atrophy in MS, and edges defined by healthy functional connectivity involving the nodes of the regions of grey matter atrophy in MS;

computing, by a processor using the AFN model, an output based on the preprocessed input, the output including network-based functional imaging output in MS (NETFIO-MS) indices indicating a progression of MS; and based on the output, providing a diagnosis of MS in response to presence of altered functional connectivity involving localized brain regions in the subject based on the application of the preprocessed input to the AFN model.

2. The method of claim 1, wherein the altered functional connectivity involving localized brain regions is determined by meta-analysis of a gray-matter atrophy pattern of MS from the AFN model and a set of functional co-activation patterns of healthy controls.

3. The method of claim 1, wherein a root mean square error of approximation of the AFN model is used to quantify MS-associated neurodegeneration.

4. The method of claim 1, wherein structural equation modeling (SEM) edge weights of the AFN model is used to quantify MS-associated neurodegeneration.

5. The method of claim 1, further comprising:

determining a treatment regimen or treatment effectiveness based on the output and diagnosis of MS; and transmitting the treatment regimen to a user.

6. The method of claim 1, wherein the input is acquired from a MRI device.

7. The method of claim 1, wherein the input is acquired from a user interface.

8. A system to select a treatment regimen for diagnosing and addressing multiple sclerosis (MS) of a subject, the system comprising:

a magnetic resonance imaging (MRI) device to provide an input including resting-state functional MRI (rsfMRI) data, of a brain of a subject; and a Network-based Functional Imaging Output in Multiple Sclerosis (NETFIO-MS) device connected to and in signal communication with the MRI device, wherein the NETFIO-MS device is configured to:

receive the input from the MRI device, preprocess the input via one or more of motion correction, B0 warping, slice timing correction, and spatial smoothing to thereby form a preprocessed input including one or more of gradient-echo fieldmap data of the rsfMRI data and T1-weighted data, apply the input to an atrophy-based functional network (AFN) model, the AFN model comprising nodes defined by regions of grey matter atrophy in MS, and edges defined by healthy functional connectivity involving the nodes of the regions of grey matter atrophy in MS, based on application of the preprocessed input to the AFN model, compute, by a processor of the NETFIO-MS device, an output including metrics of functional connectivity, the metrics of functional connectivity indicating diagnosis of MS in a subject and including NETFIO-MS indices indicating a progression of MS in the subject, determine a treatment regimen or treatment effectiveness corresponding to the output for the subject, and transmit the output and the treatment regimen or the treatment effectiveness to a user.

9. The system of claim 8, wherein the rsfMRI indicates a blood-oxygen-level dependent (BOLD) signal.

10. The system of claim 8, wherein the NETFIO-MS device includes one or more processors and a non-transitory machine readable storage medium, and wherein the non-transitory machine readable storage medium stores the AFN model and instructions, when executed by the processor, configured to apply the received input to the AFN model and determine the treatment regimen.

11. The system of claim 8, wherein the AFN model is trained to determine the output based on one or more sets of data, the one or more sets of data including a set of images, data, or video from subjects not exhibiting MS and a set of images, data, or video from subjects exhibiting various stages of MS.

12. The system of claim 11, wherein the AFN model is trained to determine whether an image includes nodes and connectivity between the nodes which indicate MS or potential for development of MS.

13. The system of claim 12, wherein the output includes an image of the subject's brain, the image including highlighted sections indicating the nodes and connectivity between the nodes.

14. The system of claim 8, wherein the output is utilized to track progression of MS in a subject diagnosed with MS and, based on progression of MS in the subject diagnosed with MS, the NETFIO-MS device further configured to:

update a previously determined treatment regimen, and transmit the updated treatment regimen to the user.

15. The system of claim 8, wherein the output indicates progression of MS in response to a previous treatment regimen.

16. A non-transitory machine-readable storage medium storing processor-executable instructions that, when executed by at least one processor, cause the at least one processor to:

in response to receipt of an input including resting-state functional MRI (rsfMRI) data preprocess the input to produce a preprocessed input include gradient-echo fieldmap data of the rsfMRI data and T1-weighted data, of a brain of a subject;

apply the preprocessed input to an atrophy-based functional network (AFN) model to produce an output, wherein the AFN model comprises nodes defined by regions of grey matter atrophy in MS, and edges defined by healthy functional connectivity involving the nodes of the regions of grey matter atrophy in MS; and wherein the output includes metrics of functional connectivity and NETFIO-MS indices indicating a progression of MS in the subject;

in response to the output produced by application of the input to the AFN model, determine whether the subject exhibits MS and duration of MS in the subject;

in response to a determination that the subject exhibits MS, determine a treatment regimen or treatment effectiveness based on the duration of MS in the subject; and transmit the treatment regimen or the treatment effectiveness to a user.

17. The non-transitory machine-readable storage medium of claim 16, wherein the metrics of functional connectivity includes model fit statistics and path correlation coefficients.

18. The non-transitory machine-readable storage medium of claim 17, wherein the model fit statistics include root mean square error of approximation (RMSEA).

19. The non-transitory machine-readable storage medium of claim 16, wherein the rsfMRI data includes a blood-oxygen-level dependent (BOLD) signal.

* * * * *